United States Patent
Fujiwara et al.

(10) Patent No.: US 9,651,774 B2
(45) Date of Patent: May 16, 2017

(54) OPTICAL SCANNING OBSERVATION APPARATUS HAVING VARIABLE SAMPLING TIME, AND METHOD AND COMPUTER READABLE STORAGE DEVICE

(71) Applicant: OLYMPUS CORPORATION, Tokyo (JP)

(72) Inventors: Masato Fujiwara, Tokyo (JP); Atsuyoshi Shimamoto, Tokyo (JP); Junichi Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 146 days.

(21) Appl. No.: 14/340,740

(22) Filed: Jul. 25, 2014

(65) Prior Publication Data
US 2014/0332677 A1  Nov. 13, 2014

Related U.S. Application Data

(63) Continuation of application No. PCT/JP2013/000394, filed on Jan. 25, 2013.

(30) Foreign Application Priority Data

Jan. 26, 2012 (JP) .................................. 2012-014326

(51) Int. Cl.
*G02B 26/10* (2006.01)
*G02B 23/26* (2006.01)
(Continued)

(52) U.S. Cl.
CPC .......... *G02B 26/10* (2013.01); *A61B 1/00006* (2013.01); *A61B 1/00172* (2013.01);
(Continued)

(58) Field of Classification Search
CPC ................................ G02B 26/10; G01J 1/4237
(Continued)

(56) References Cited

U.S. PATENT DOCUMENTS 4,736,110 A   4/1988   Awamura
6,294,775 B1  9/2001   Seibel et al.
(Continued)

FOREIGN PATENT DOCUMENTS

JP    S62-5791 A       1/1987
JP    2005-215357 A    8/2005
(Continued)

OTHER PUBLICATIONS

Extended Supplementary European Search Report dated Oct. 9, 2015 from related European Application No. 13 74 1514.7.
(Continued)

*Primary Examiner* — Seung C Sohn
(74) *Attorney, Agent, or Firm* — Scully, Scott, Murphy & Presser, PC

(57) ABSTRACT

Provided is an optical scanning observation apparatus including: a light source unit (30) for outputting laser light; a scanning part (23) for scanning, on an object of observation (70), a condensing position of the laser light output from the light source; and a detection unit (40) for sampling signal light obtained through scanning of the laser light, and converting the signal light into an electric signal, in which a sampling time for detecting signal light per one sampling is varied in accordance with changes in scanning rate of the scanning part (24) scanning on the object of observation (70). In this manner, variation in resolution of an image resulting from changes in scanning rate per each sampling can be reduced.

17 Claims, 17 Drawing Sheets

(51) Int. Cl.
  *G02B 23/24* (2006.01)
  *A61B 1/00* (2006.01)
  *G01J 1/42* (2006.01)
  *A61B 1/06* (2006.01)
  *H04N 5/235* (2006.01)

(52) U.S. Cl.
  CPC ............ *A61B 1/063* (2013.01); *G01J 1/4257* (2013.01); *G02B 23/2469* (2013.01); *G02B 23/26* (2013.01); *G02B 26/103* (2013.01); *H04N 5/2354* (2013.01)

(58) Field of Classification Search
  USPC ......................................................... 250/234
  See application file for complete search history.

(56) References Cited

U.S. PATENT DOCUMENTS

| | | | | |
|---|---|---|---|---|
| 2009/0185034 | A1* | 7/2009 | Kishida | ................ G02B 21/365 348/79 |
| 2010/0157039 | A1 | 6/2010 | Sugai | |
| 2011/0037841 | A1 | 2/2011 | Shibasaki | |
| 2012/0176502 | A1* | 7/2012 | Usui | ................ H04N 5/23241 348/211.99 |

FOREIGN PATENT DOCUMENTS

| | | |
|---|---|---|
| JP | 2005-321531 A | 11/2005 |
| JP | 2007-034052 A | 2/2007 |
| JP | 2007-114505 A | 5/2007 |
| JP | 2008-015030 A | 1/2008 |
| JP | 2010-142482 A | 7/2010 |
| JP | 2010-142597 A | 7/2010 |
| JP | 2010-284189 A | 12/2010 |

OTHER PUBLICATIONS

Chinese Office Action dated Dec. 28, 2015 from related Chinese Patent Application No. 201380006683.5, together with an English language translation.
Japanese Office Action dated Jul. 12, 2016 in related Japanese Patent Application No. 2013-555210.
Chinese Office Action dated Aug. 8, 2016 in related Chinese Patent Application No. 201380006683.5.
Japanese Office Action dated Nov. 8, 2016 in related Japanese Patent Application No. 2013-555210.
Chinese Office Action dated Feb. 15, 2017 in Chinese Patent Application No. 201380006683.5.

* cited by examiner

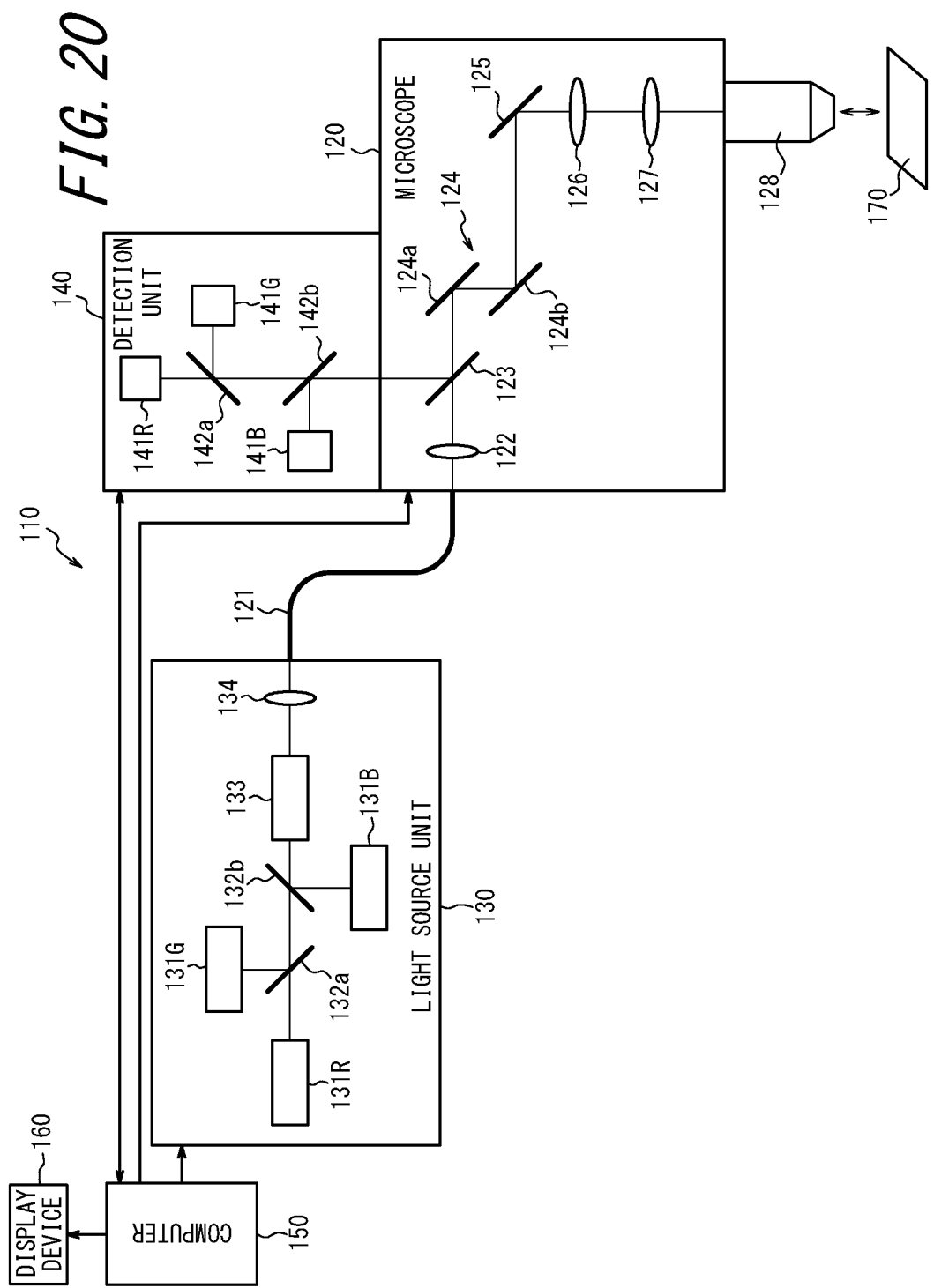

OPTICAL SCANNING OBSERVATION APPARATUS HAVING VARIABLE SAMPLING TIME, AND METHOD AND COMPUTER READABLE STORAGE DEVICE

CROSS REFERENCE TO RELATED APPLICATION

The present application is a Continuing Application based on International Application PCT/JP2013/000394 filed on Jan. 25, 2013, which, in turn, claims the priority from Japanese Patent Application No. 2012-14326 filed on Jan. 26, 2012, the entire disclosure of these earlier applications being herein incorporated by reference.

TECHNICAL FIELD

The present invention relates to an optical scanning observation apparatus in which non-uniformity in resolution resulting from varying scanning rate within an observation range is reduced.

BACKGROUND ART

Conventionally, there has been known an optical scanning observation apparatus which irradiates an object of observation with laser light and scans the irradiation position thereof, so as to convert into electric signals, using a photoelectric conversion means, signal lights including transmitted light, reflected light, and fluorescence light obtained from the object of observation, to thereby form image data. Examples of the apparatus may include: a laser scanning microscope using a galvanometer scanner as the scanning mechanism; and an optical scanning endoscope which irradiates an object of observation with laser light emitted from a fiber in such a manner as to form a spot on the object of observation, and oscillates the fiber so as to scan the laser light on the object of observation, to thereby acquire signal light to form an image.

In the scanning mechanism employed in the aforementioned optical scanning observation apparatuses, the scanning rate (scanning line rate) at the irradiation point on the object of observation may not necessarily stay constant, depending on the control method and the scanning pattern of the mechanism. For example, in a scanning mechanism which is oscillated at a resonance frequency in a uniaxial direction, the movement of the scanning mechanism in the oscillating direction is controlled according substantially to a sinusoidal function, and thus the scanning rate on the object of observation does not stay constant. Meanwhile, spiral scanning of an object of observation is characterized in that the scanning rate becomes higher with increasing distance from the scanning center or drawing closer to the periphery of the screen.

In general, in optical disks including CD and DVD, the disk rotation speed is adjusted depending on the distance from the disk center so as to keep the scanning rate constant, to thereby ensure the uniform recording density. However, in the case of a laser scanning microscope or an optical scanning endoscope where the scanning mechanism is operated at high speed using a resonance frequency, it often involves difficulty to maintain a constant scanning rate by adjusting the frequency depending on the scanning position.

When the scanning rate varies, brightness within the scanning range becomes non-uniform unless the rest of the conditions is changed. In light thereof, there has been proposed a method of adjusting the power of laser light so as to make it uniform the irradiation density within the scanning range, to thereby reduce non-uniformity in brightness (see, for example, Patent Literature 1).

Alternatively, in a case where the scanning rate varies while the sampling frequency is kept constant, the number of sampling points per unit area is high in a region with a low scanning rate, which means that the scanning is wastefully performed. In contrast, in a region with a high scanning rate, the number of sampling points per unit area is so small, which may cause inconvenience where no sampling point can be found within a pixel. In light thereof, there has been disclosed a method of keeping substantially constant the sampling density within the scanning range, to thereby avoid such problems (see, for example, Patent Literature 2).

CITATION LIST

Patent Literature

PTL 1: JP 2008-15030 A
PTL 2: JP 2010-142482 A

SUMMARY OF INVENTION

In order to attain the aforementioned object, an optical scanning observation apparatus according to a first aspect of the present invention includes:

a light source for outputting laser light;

a scanning mechanism for scanning, on an object of observation, a condensing position of the laser light output from the light source; and a detector for sampling signal light obtained through the scanning of the laser light, and converting the signal light into an electric signal;

in which, in accordance with changes in scanning rate of the scanning mechanism scanning on the object of observation, sampling time for detecting the signal light per one sampling is varied.

According to a second aspect of the present invention, in the optical scanning observation apparatus according to the first aspect, within a scanning range on the object of observation, the sampling time at the scanning rate taking a minimum value is represented as $t_{vmin}$, and the sampling time at the scanning rate taking a maximum value is represented as $t_{vmax}$, the $t_{vmin}$ and the $t_{vmax}$ satisfying a conditional expression (1).

$$t_{vmin} > t_{vmax} \tag{1}$$

According to a third aspect of the present invention, in the optical scanning observation apparatus according to the second aspect, the $t_{vmin}$ and the $t_{vmax}$ satisfy a conditional expression (2):

[Expression 1]

$$0.5 \le \frac{v_{max} \times t_{vmax}}{v_{min} \times t_{vmin}} \le 2, \tag{2}$$

where $v_{max}$ and $v_{min}$ each represent a maximum value and a minimum value of the scanning rate, respectively, within the scanning range on the object of observation.

According to a fourth aspect of the present invention, in the optical scanning observation apparatus according to any of the first to third aspects, within the scanning range on the object of observation, the scanning rate is represented as v, the sampling time is represented as t, and the product of the scanning rate and the sampling time has a maximum value represented as max(v× t) and a minimum value represented as min(v×t), the max (v×t) and the min(v×t) satisfying a conditional expression (3).

[Expression 2]

$$1 \le \frac{\max(v \times t)}{\min(v \times t)} \le 2 \qquad (3)$$

According to a fifth aspect of the present invention, in the optical scanning observation apparatus according to the first aspect, within the scanning range on the object of observation, the sampling time is varied such that the product with the scanning rate is maintained substantially at a constant value.

According to a sixth aspect of the present invention, in the optical scanning observation apparatus according to any of the first to fifth aspects, the sampling time is defined by at least one of the detection time of the detector per one sampling and the irradiation time for emitting the laser light by the light source per one sampling.

According to a seventh aspect of the present invention, in the optical scanning observation apparatus according to any of the first to sixth aspects, the laser light output from the light source is varied in power in accordance with changes in scanning rate of the scanning mechanism scanning on the object of observation.

According to an eighth aspect of the present invention, in the optical scanning observation apparatus according to the seventh aspect, within the scanning range on the object of observation, the laser light has a power represented as $p_{vmin}$ when the scanning rate takes a minimum value, and the laser light has a power represented as $p_{vmax}$ when the scanning rate takes a maximum value, the $p_{vmin}$ and the $p_{vmax}$ satisfying a conditional expression (4).

$$p_{vmin} < p_{vmax} \qquad (4)$$

According to a ninth aspect of the present invention, in the optical scanning observation apparatus according to the seventh aspect, the $p_{vmin}$ and the $p_{vmax}$ satisfy a conditional expression (5):

[Expression 3]

$$0.5 \le \frac{p_{vmin}/v_{min}}{p_{vmax}/v_{max}} \le 2, \qquad (5)$$

where $v_{max}$ and $v_{min}$ each represent a maximum value and a minimum value of the scanning rate, respectively, within the scanning range on the object of observation.

According to a tenth aspect of the present invention, in the optical scanning observation apparatus according to any of the first to sixth aspects, the detector is varied in detection sensitivity for detecting the signal light, in accordance with changes in scanning rate of the scanning mechanism scanning on the object of observation.

According to an eleventh aspect of the present invention, in the optical scanning observation apparatus according to the tenth aspect, within the scanning range on the object of observation, the detection sensitivity at the scanning rate taking a minimum value is represented as $s_{vmin}$ and the detection sensitivity at the scanning rate taking a maximum value is represented as $s_{vmax}$, the $s_{vmin}$ and the $s_{vmax}$ satisfying a conditional expression (6).

$$s_{vmin} < s_{vmax} \qquad (6)$$

According to a twelfth aspect of the present invention, in the optical scanning observation apparatus according to the eleventh aspect, the $s_{vmin}$ and the $s_{vmax}$ satisfy a conditional expression (7):

[Expression 4]

$$0.5 \le \frac{s_{min}/v_{min}}{s_{max}/v_{max}} \le 2, \qquad (7)$$

where $v_{max}$ and $v_{min}$ each represent a maximum value and a minimum value of the scanning rate, respectively, within the scanning range on the object of observation.

According to a thirteenth aspect of the present invention, in the optical scanning observation apparatus according to any of the first to twelfth aspects, a sampling interval is varied in accordance with changes in scanning rate of the scanning mechanism scanning on the object of observation.

According to a fourteenth aspect of the present invention, in the optical scanning observation apparatus according to the thirteenth aspect, within the scanning range on the object of observation, the sampling interval at the scanning rate taking a minimum value is represented as $t_{s-vmin}$ and the sampling interval at the scanning rate taking a maximum value is represented as $t_{s-vmax}$, the $t_{s-vmin}$ and the $t_{s-vmax}$ satisfying a conditional expression (8).

$$t_{s-vmax} < t_{s-vmin} \qquad (8)$$

According to a fifteenth aspect of the present invention, in the optical scanning observation apparatus according to any of the first to fourteenth aspects, the scanning mechanism spirally scans on the object of observation.

BRIEF DESCRIPTION OF DRAWINGS

The present invention will be further described below with reference to the accompanying drawings, wherein:

FIG. 20 is a block diagram illustrating a schematic configuration of a laser scanning microscope apparatus as an example of an optical scanning observation apparatus according to a third embodiment of the present invention.

DESCRIPTION OF EMBODIMENTS

In the following, embodiments of the present invention will be described with reference to the drawings.

First Embodiment

Figure 1:
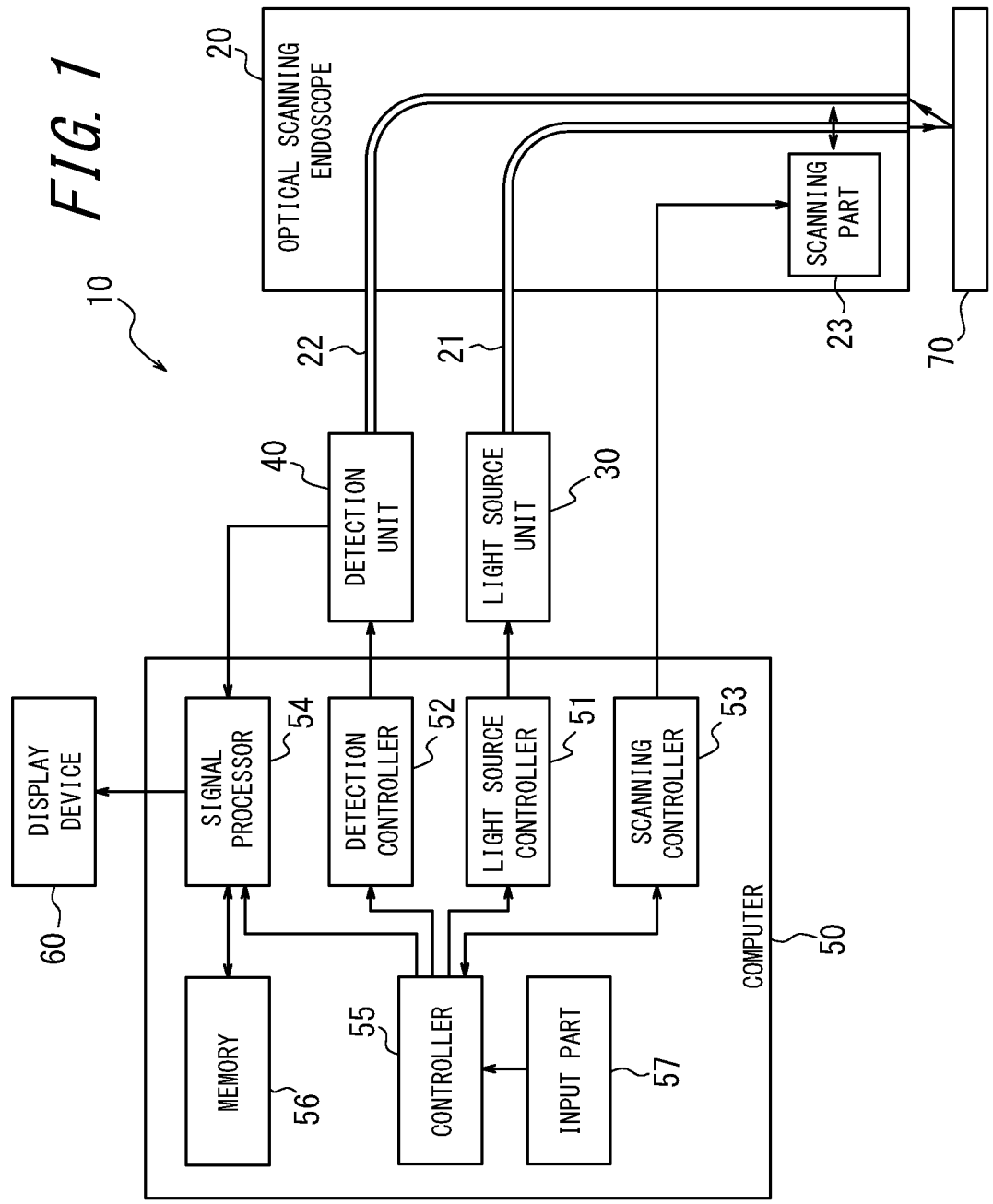
FIG. 1 is a block diagram illustrating a schematic configuration of an optical scanning endoscope apparatus as an example of an optical scanning observation apparatus according to a first embodiment of the present invention.

FIG. 1 is a block diagram illustrating a schematic configuration of an optical scanning endoscope apparatus 10 as an example of an optical scanning observation apparatus according to a first embodiment of the present invention. The optical scanning endoscope apparatus 10 is configured by including: an optical scanning endoscope (main body) 20; a light source unit 30 (light source); a detection unit 40 (detector); a computer 50; and a display device 60. The light source unit 30 and the optical scanning endoscope 20 are optically connected to each other via a SMF (single-mode fiber) 21, while the detection unit 40 and the optical scanning endoscope 20 are optically connected to each other via a plurality of MMFs (multi-mode fibers) 22.

Figure 2:
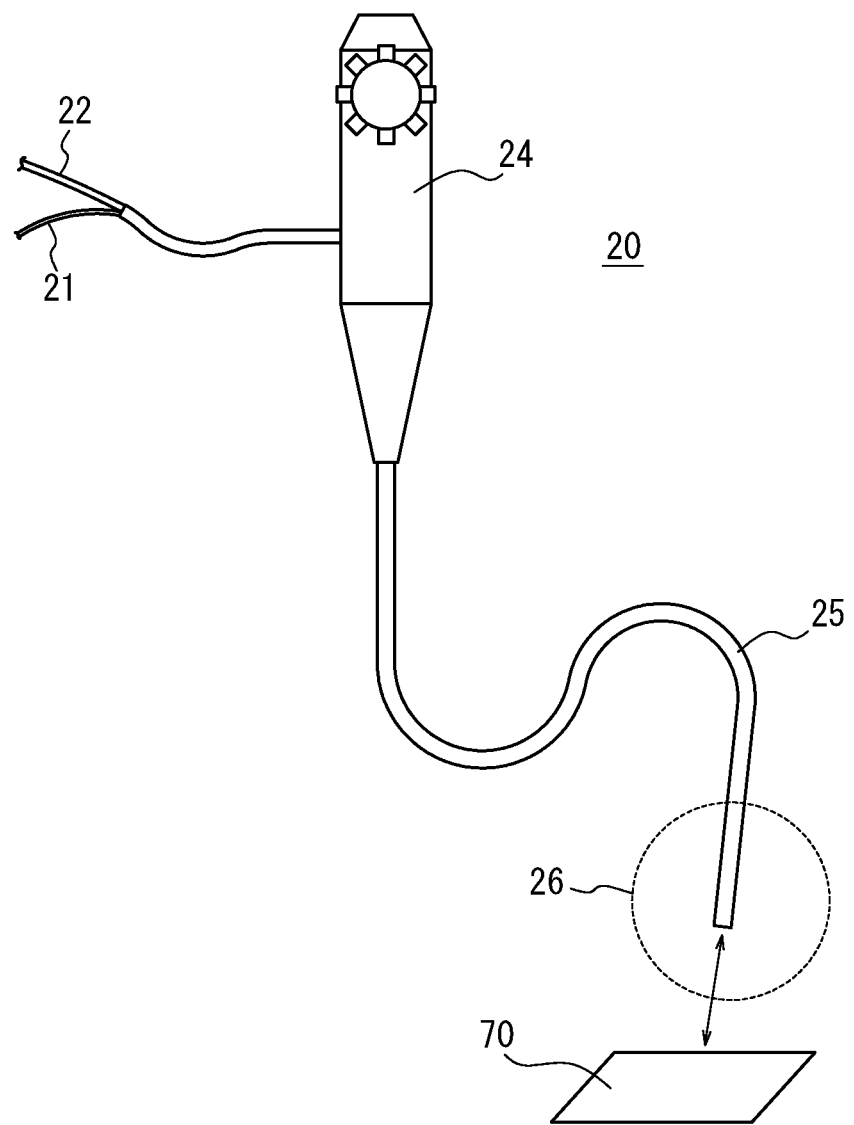
FIG. 2 is an overview diagram schematically illustrating the optical scanning endoscope (main body) of FIG. 1.

FIG. 2 is an overview diagram schematically illustrating the optical scanning endoscope (main body) 20. The optical scanning endoscope (main body) 20 includes an operation part 24, an insertion part 25, and a tip part 26. The tip part 26 is connected with the SMF 21 extending from the light source unit 30 and with MMFs 22 extending from the detection unit 40, the SMF 21 and the MMFs 22 being guided to the tip part 26 through the insertion part 25.

Figure 3:
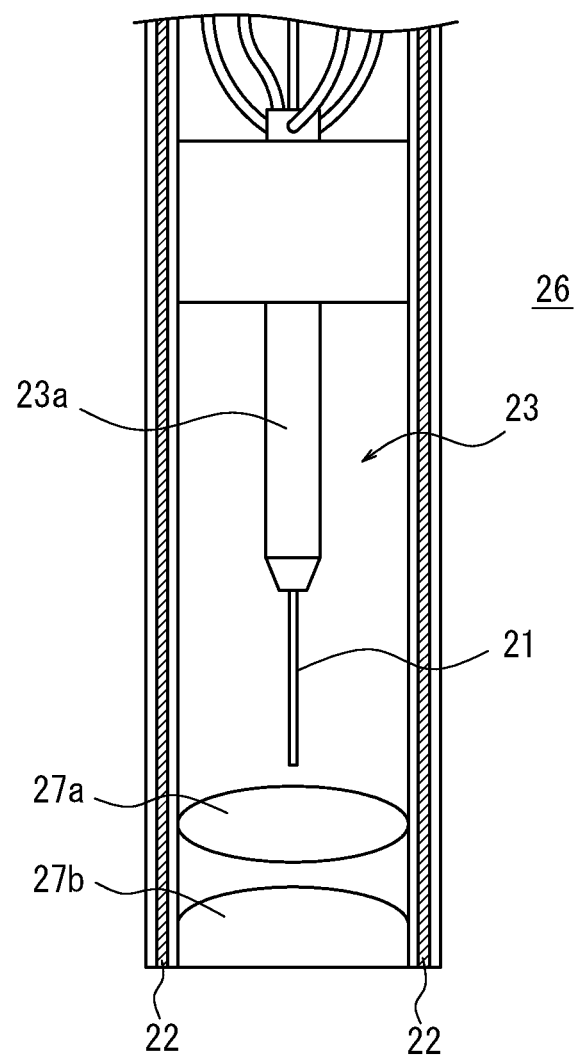
FIG. 3 is an enlarged sectional diagram illustrating the tip part of the optical scanning endoscope (main body) of FIG. 2.

FIG. 3 is an enlarged sectional diagram illustrating the tip part 26 of the optical scanning endoscope (main body) 20 of FIG. 2. The SMF 21 is disposed to pass through the center of the tip part 26, and the MMFs 22 are disposed to pass through the outer circumference of the tip part 26. The tip end of the SMF 21 is held movable to a slight extent without being fixed. Two lenses 27a and 27b are disposed ahead of the emitting end of the SMF 21 so that the SMF 21 is configured to output a laser light that forms a small spot on an object of observation 70. Here, the two lenses 27a, 27b illustrated in FIG. 3 may be configured as a single lens or as a plurality of lenses. Meanwhile, the incident end of each of the MMFs 22 faces to the side where the object of observation 70 is disposed, so that light obtained by irradiating the object of observation 70 with laser light output from the SMF 21 is configured to be incident as signal light onto the incident end of the MMF 22. Here, the light obtained by irradiating the object of observation include, for example, a reflected light of the laser light output from the SMF 21 or fluorescence light generated through the irradiation of laser light.

Provided at the tip end of the SMF 21 is a scanning part 23 (scanning mechanism) having a piezoelectric element 23a. The piezoelectric element 23a includes two pairs of piezoelectric elements disposed as being opposed to each other across the SMF 21, and the piezoelectric elements each may be applied with voltage so as to have the SMF 21 tilted in two directions including a first direction and a second direction, the first and second directions being radial directions of the SMF 21 as being orthogonal to each other. The scanning part 23 is electrically connected to a scanning controller 53 of the computer 50 of FIG. 1 to be described later.

Figure 4:
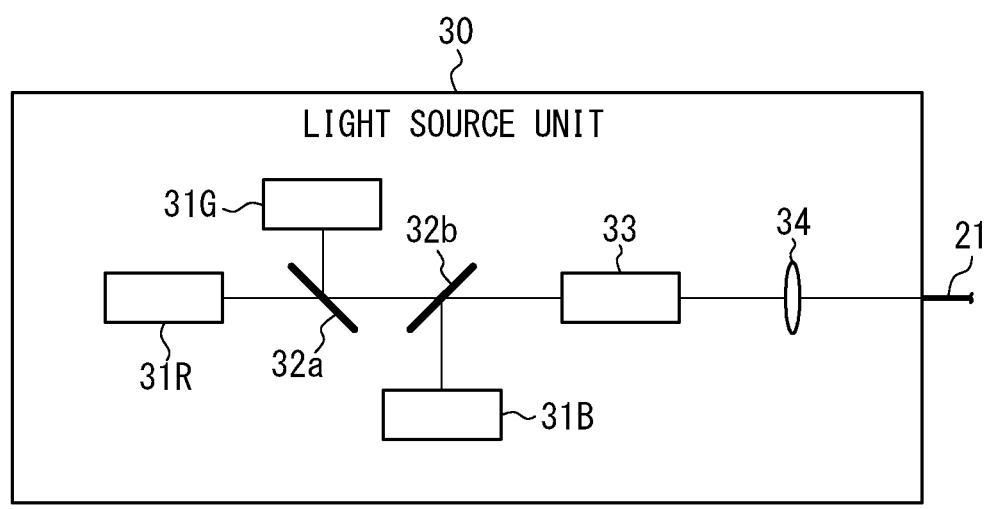
FIG. 4 is a diagram illustrating a schematic configuration of the light source unit of the optical scanning endoscope apparatus of FIG. 1.

FIG. 4 is a diagram illustrating a schematic configuration of the light source unit 30 of the optical scanning endoscope apparatus 10 of FIG. 1. The light source unit 30 includes: laser sources 31R, 31G, 31B for emitting CW (continuous wave) laser lights of three primary colors of red, green, and blue; dichroic mirrors 32a, 32b; an AOM (acousto-optic modulator) 33; and a lens 34. As the laser source 31R for red, for example, a LD (laser diode) may be used. As the laser source 31G for green, for example, a DPSS laser (semiconductor-pumped solid-state laser) may be used. Further, as the laser source 31B for blue, for example, a LD may be used.

The laser source 31R and the laser source 31G are disposed such that the laser light emitted from the laser source 31R has an optical path that intersects, at a predetermined point, with the optical path of a laser light emitted from the laser source 31G, and the dichroic mirror 32a is disposed at the point of intersection of the optical paths. The dichroic mirror 32a has optical characteristics for transmitting light in the red wavelength range while reflecting light in the green wavelength range, and is disposed at an angle for multiplexing: a red laser light that has been emitted from the laser source 31R and transmitted through the dichroic mirror 32a; and a green laser that has been emitted from the laser source 31G and reflected by the dichroic mirror 32a.

Further, the laser source 31B is disposed such that the blue laser light emitted from the laser source 31B has an optical path that intersects, at a predetermined point, with the optical path of a laser light obtained by multiplexing the red laser light and the green laser light, and the dichroic mirror 32b is disposed at the point of intersection of the optical paths. The dichroic mirror 32b has optical characteristics for transmitting lights in the red wavelength range and in the green wavelength range while reflecting light in the blue wavelength range, and is disposed at an angle for multiplexing: a laser light that has been multiplexed by the dichroic mirror 32a and transmitted through the dichroic mirror 32b; and the blue laser light that has been emitted from the laser source 31B and reflected by the dichroic mirror 32b. In this manner, the laser lights of three primary colors of red, green, blue each emitted from the laser sources 31R, 31G, 31B, respectively, are multiplexed to be obtained as a white laser light.

The AOM 33 is an element for subjecting incident light to intensity modulation, and is capable of switching between the light-shielding state and the light-transmitting state at high speeds. The white laser light multiplexed by the dichroic mirrors 32a, 32b passes through the AOM 33 when the AOM 33 is in the light-transmitting state, and is caused to be incident on the incident end of the SMF 21 through the lens 34. The AOM 33 is electrically connected to a light source controller 51 of the computer 50 to be described later of FIG. 1. The laser sources 31R, 31G, and 31B, and the dichroic mirrors 32a and 32b may be arbitrarily arranged without being limited thereto; they may be arranged so that, for example, green and blue laser lights may be multiplexed before being multiplexed with the red laser light.

Figure 5:
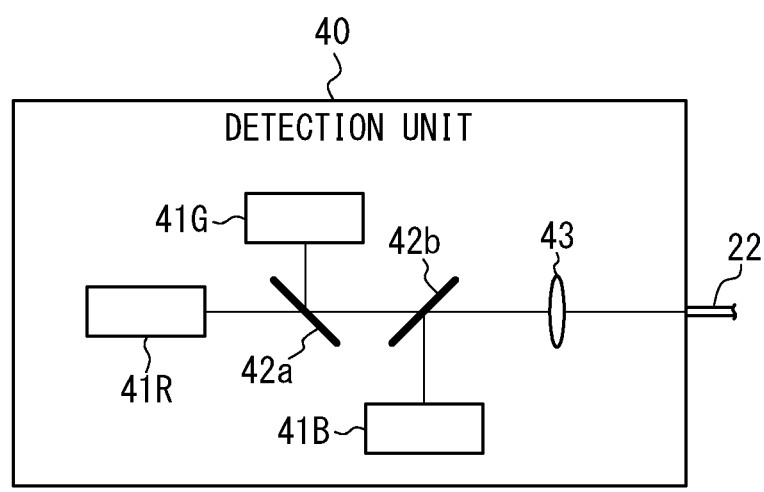
FIG. 5 is a diagram illustrating a schematic configuration of the detection unit of the optical scanning endoscope apparatus of FIG. 1.

FIG. 5 is a diagram illustrating a schematic configuration of the detection unit 40 of the optical scanning endoscope apparatus 10 of FIG. 1. The detection unit 40 includes: photodetectors 41R, 41G, 41B, that use photodiodes for detecting light corresponding to each color of red, green, and blue; dichroic mirrors 42a, 42b; and a lens 43. The detection unit 40 has a plurality of the MMFs 22 connected thereto in a bundle.

Signal lights reflected or generated by the object of observation 70 irradiated with laser light pass through the MMFs 22 to be emitted from the emitting end thereof, which are then converted into substantially parallel light fluxes through the lens 43. On the optical path of the signal lights converted into substantially parallel light fluxes, the dichroic mirrors 42a and 42b are disposed on as being tilted relative to the optical path direction. The dichroic mirror 42b has optical characteristics for reflecting light in the blue wavelength range while transmitting light in the red and green wavelength ranges, and separates a blue signal light from the signal lights converted into parallel light fluxes through the lens 43. The blue signal light thus separated is detected by the photodetector 41B and converted into an electric signal. The dichroic mirror 42a has optical characteristics for reflecting light in the green wavelength range while transmitting light in the red wavelength range, and separates the signal light transmitted through the dichroic mirror 42b into a red signal light and a green signal light. The red and green signal lights thus separated are each detected by the photodetector 41R and the photodetector 41G, respectively, and converted into an electric signal.

Here, the photodetectors 41R, 41G, and 41B are electrically connected to a detection controller 52 and a signal processor 54 of the computer 50 to be described later of FIG. 1. The photodetectors 41R, 41G, and 41B, and the dichroic mirrors 42a and 42b may be arbitrarily arranged without being limited thereto; they may be arranged so that, for example, a red light may be separated from the signal lights and then the remaining signal lights may be separated into green and blue signal lights.

The computer 50 of FIG. 1 drive controls the scanning part 23, the light source unit 30, and the detection unit 40 of the optical scanning endoscope (main body) 20 while processing electric signals output from the detection unit 40 to synthesize an image and output the image to the display device 60. Accordingly, the computer 50 includes: the light source controller 51, the detection controller 52; the scanning controller 53; the signal processor 54; a controller 55; a memory 56; and an input part 57.

The light source controller 51 may control the AOM 33 of the light source unit 30, so as to adjust the intensity of laser light incident on the SMF 21. The light source controller 51 is capable of switching the AOM 33 between the light-shielding state and the light-transmission state. In this case, the AOM 33 is controlled to be switched to the light-transmission state when irradiating the object of observation 70 with laser light, while the AOM 33 is controlled to be switched to the light-shielding state when irradiating no laser light.

The detection controller 52 is capable of controlling the detection timing, the detection time, and the detection sensitivity at which the signal lights are detected by the photodetectors 41R, 41G, 41B of the detection unit 40.

Figure 6:
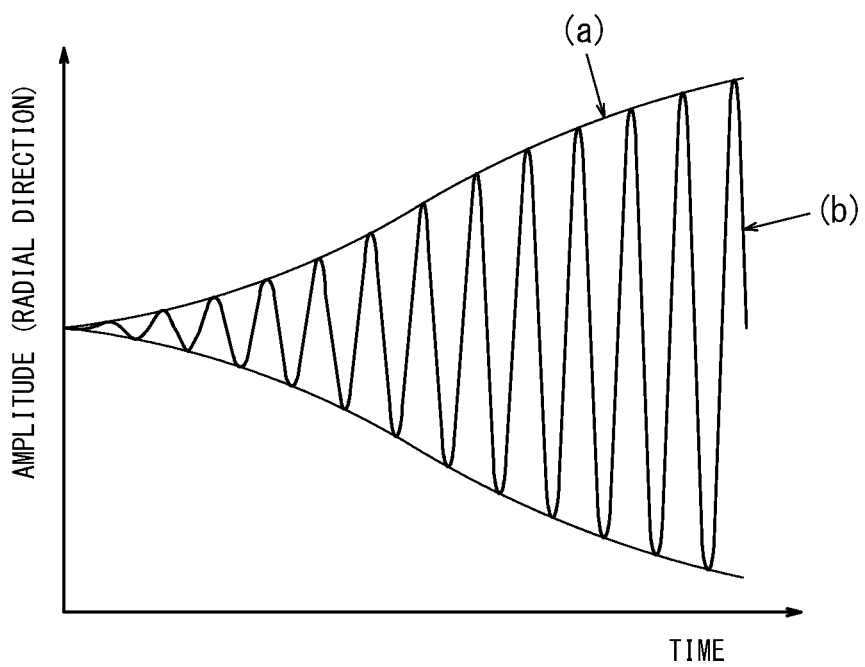
FIG. 6 is a graph showing an example of temporal change in amplitude during spiral scanning on an object of observation.

The scanning controller 53 drive controls the scanning part 23 of the optical scanning endoscope (main body) 20, so as to spirally scan the object of observation with a spot of a laser light emitted from the SMF 21. Specifically, the piezoelectric element 23a of the scanning part 23 is applied with an alternating voltage so as to be oscillated at a resonance frequency f of the tip end of the SMF 21 in two mutually-orthogonal directions each being perpendicular to the optical axes of the lenses 27a, 27b, as being phase-shifted by 90 degrees from each other. The alternating voltage may be varied according to a predetermined pattern, to thereby change the amplitude, as shown in FIG. 6 by way of example. FIG. 6 shows: (a) a radial movement of the spot of the laser light in one of the aforementioned two mutually-orthogonal directions; and (b) the diameter of the spiral path. The spiral scanning for sampling is performed by repeating an operation where the scanning is performed from an amplitude of substantially 0 to a predetermined maximum amplitude where the sampling is stopped to attenuate the amplitude to almost 0, and then the scanning for sampling is started again. In this manner, the object of observation can be scanned along a spiral path.

The signal processor 54 generates image data corresponding to each sampling point, based on the electric signals output from the photodetectors 41R, 41G, 41B of the detection unit 40, and stores the image data as pixel data corresponding thereto, in the memory 56. Here, the signal processor 54 refers to a scanning start signal from the controller 55, and estimates the position of the sampling point based on the time elapsed from the start of spiral scanning.

The signal processor 54 stores, for each spiral scanning for sampling, pixel data associated with the positions of the sampling points on the object of observation 70, in the memory 56. Further, the signal processor 54 performs interpolation processing after the scanning for sampling, to thereby estimate data on pixels that have not been acquired, so as to generate an image of the object of observation 70 and display the image on the display device 60.

The controller 55 controls, as a whole, the light source controller 51, the detection controller 52, the scanning controller 53, and the signal processor 54 of the optical scanning endoscope apparatus 10 in a synchronized manner, to thereby cause the object of observation 70 to be spirally-scanned with laser light from the light source unit 30, cause the detection unit 40 to convert signal light obtained from the object of observation 70 into an electric signal at a predetermined timing and detection time, and cause the signal processor 54 to generate image data.

The detection time per one sampling by the detection unit 40 and/or the irradiation time of laser light emitted by the light source unit 30 per one sampling through the control of the AOM 33 may not be constant in value during the spiral scanning for sampling, and may be varied in accordance with changes in scanning rate of the scanning part 23 scanning on the object of observation 70. The sampling time per one sampling in the scanning for sampling is defined by one or both of the detection time per one sampling by the detection unit 40 and the irradiation time of laser light emitted by the light source unit 30 per one sampling. For example, when the light source unit 30 is always in the light-transmitting state, the sampling time becomes equal to the detection time of the detection unit 40. When the irradiation time of laser light emitted from the light source unit 30 is varied within a time frame of the detection time of the detection unit 40, the sampling time becomes equal to the irradiation time of laser light.

Further, the power of laser light emitted from the light source unit 30 or the detection sensitivity of the detection unit 40 detecting signal light may not be constant in value during the spiral scanning for sampling, and may be varied in accordance with changes in scanning rate of the scanning part 23 scanning on the object of observation 70. The intensity of laser light from the light source 30 is adjusted through the control of the AOM 33.

Further, the sampling interval in the scanning for sampling may not be constant in value during the spiral scanning for sampling, and may be varied in accordance with changes in scanning rate of the scanning part 23 scanning on the object of observation 70. The sampling interval may be varied by changing the irradiation interval of laser light, i.e., the interval of switching the laser light output from the light source unit 30 through the control of the AOM 33 between the light-shielding state and the light-transmitting state, and/or changing the period of detecting signal light by the detection unit 40.

To control the aforementioned detection time, detection sensitivity, and detection interval of the detection unit 40, the irradiation time of laser light output from light source unit 30, the power of the laser light, and the interval of irradiating laser light, the light source controller 51 and the detection controller 52, or the controller 55 may store a pattern predetermined in accordance with the time elapsed from the start of the spiral scanning, or alternatively, the user of the optical scanning endoscope apparatus 10 may define parameters to be changed and the profile of the change through the input part 57, so as to carry out the control through the control of the controller 55.

The detection time, detection interval, and detection sensitivity of the photodetectors 41R, 41G, 41B, the irradiation time of laser light emitted from the light source unit 30 through the control of the AOM 33, and the power and irradiation interval of the laser light may not be constant in value during the spiral scanning for sampling, and may be varied in accordance with changes in scanning rate of the scanning part 23 scanning on the object of observation 70. To implement such changes, a predetermined pattern may be stored in the light source controller 51 and in the detection controller 52, or alternatively, the user of the optical scanning endoscope apparatus 10 may define parameters to be varied so that the changes can be made under the control of the controller 55.

The optical scanning endoscope apparatus 10 configured as described above according to the first embodiment may be operated as follows.

(Adjustment of Sampling Time)

First, in the optical scanning endoscope apparatus 10, the object of observation 70 is rotary-scanned at a resonance frequency f of the tip end of the SMF 21. The scanning rate v can be represented by the equation (9), where $r_c$ represents the distance from the scanning center C and $\omega(\omega=2\pi f)$ represents an angular resonance frequency. The use of the resonance frequency allows for scanning at high oscillation frequency.

$$v = r_c \times \omega \qquad (9)$$

The resonance frequency f is constant in value irrespective of the scanning position, and thus, the scanning rate increases with the increasing distance $r_c$ from the scanning center. Here, assuming that the sampling time t and the sampling interval $t_s$ are controlled to be constant in value, the scanning distance ($d_s$) to be scanned for one sampling is obtained as follows:

$$r_c \times \omega \times t, \text{ and}$$

the distance between samplings (sampling interval distance: $d_i$) is obtained as follows:

$$r_c \times \omega \times t_s.$$

Figure 7:
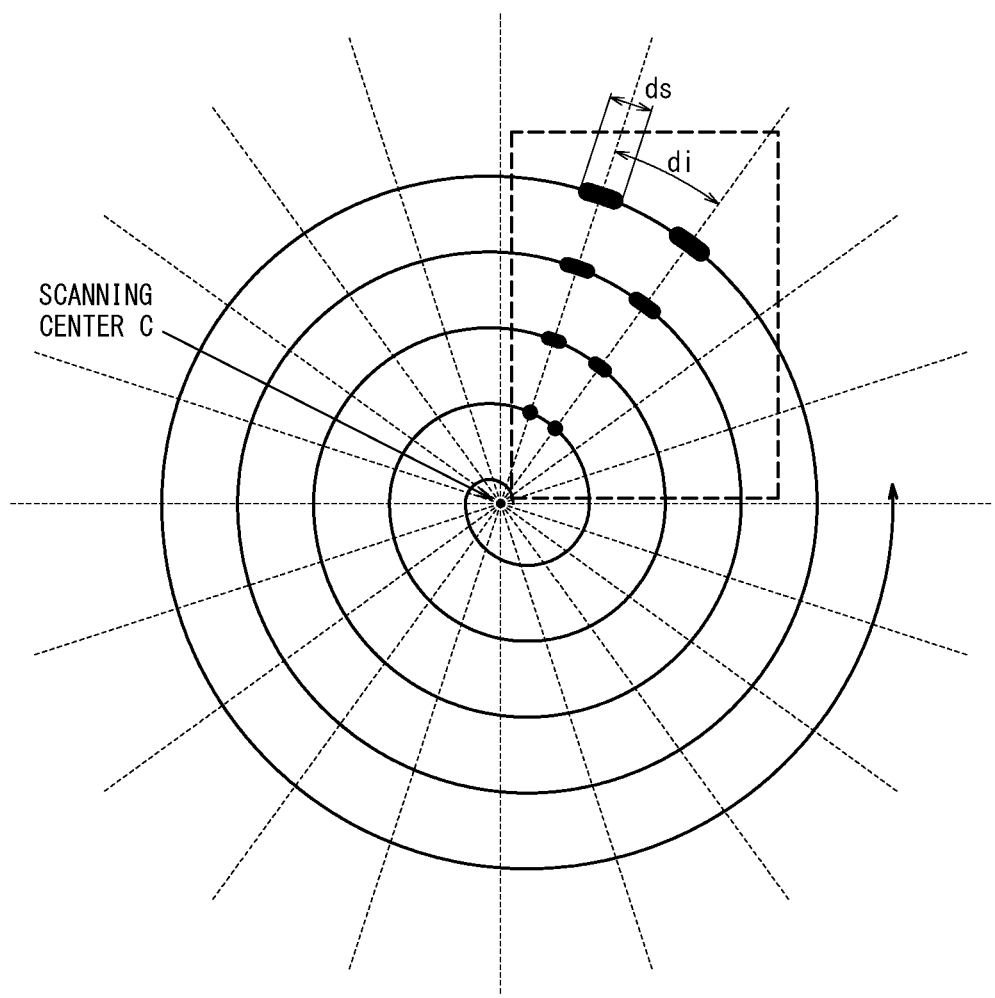
FIG. 7 is a diagram illustrating a spiral scanning for sampling according to a conventional example.

FIG. 7 is a diagram illustrating the spiral scanning for sampling performed while keeping the sampling time and the sampling interval constant as described above. The black dots represent sampling points. The scanning distance $d_s$ (the length of the sampling point in the circumferential direction) for one sampling becomes longer with the increasing distance $r_c$ from the scanning center. For this reason, if the sampling time is defined based on the pixel size at a position closer to the scanning center, a region to be defined by a sampling point per one sampling in the outer periphery disadvantageously extends in the circumferential direction across a plurality of pixels, which causes image blur to reduce resolution. On the other hand, if the sampling time and the sampling interval are defined to fit the conditions in the outer periphery, sampling at a position closer to the scanning center must be performed at a density higher than the pixel density, which means that detection unnecessary for image formation is inadvertently performed many times.

In view of the above, according to the first embodiment, the sampling time t is varied along with the changes in scanning rate. More specifically, the sampling time t is changed to be shorter when the scanning rate is higher. The conditional expression (1) may be satisfied, where $t_{vmin}$ represents the sampling time at a minimum scanning rate and $t_{vmax}$ represents the sampling time at a maximum scanning rate within the scanning range on the object of observation 70, so that the degradation in resolution that would occur along with an increase in scanning rate from at the maximum scanning rate relative to at least the minimum scanning rate can be reduced, as compared with the case where the sampling time t is kept constant.

$$t_{vmin} > t_{vmax} \qquad (1)$$

Further, $t_{vmin}$ and $t_{vmax}$ preferably satisfy the conditional expression (2), where $v_{max}$ and $v_{min}$ each represent a maximum value and a minimum value of the scanning rate, respectively, within the scanning range on the object of observation 70.

[Expression 5]

$$0.5 \leq \frac{v_{max} \times t_{vmax}}{v_{min} \times t_{vmin}} \leq 2 \quad (2)$$

As long as $t_{vmin}$ and $t_{vmax}$ fall within a range satisfying the conditional expression (2), the range of difference in scanning distance at a maximum scanning rate can be held within twice of at least the scanning distance at a minimum scanning rate. If the range of difference in scanning distance is twice or more, the resolution in sampling is degraded near the outer periphery in the scanning range, in particular, when the object of observation 70 is spirally-scanned, which is not preferred because the degradation in resolution becomes more conspicuous near the outer periphery of the screen when the aberration of an optical system including a lens is also taken into consideration. Meanwhile, the difference in scanning distance is defined to be at least 0.5, so as to prevent $t_{vmax}$ from being reduced to so short that it requires a high-performance detector, and further to prevent the quantity of light from becoming so small that it requires a detector of higher sensitivity and higher image resolution.

Further, the conditional expression (3) may preferably be satisfied, where v represents the scanning rate and t represents the sampling time in the scanning range on the object of observation 70, and max(v×t) and min(v×t) each represent a maximum value and a minimum value, respectively, of a product of the scanning rate and the sampling time.

[Expression 6]

$$1 \leq \frac{\max(v \times t)}{\min(v \times t)} \leq 2 \quad (3)$$

When the conditional expression (3) is satisfied, the product of the scanning rate and the sampling time (v×t), i.e., the range of variation in distance to be scanned in one sampling, can be held within twice. As long as the range of variation in distance can be kept to this extent, the obtained image would have not so much blur caused therein.

Figure 8:
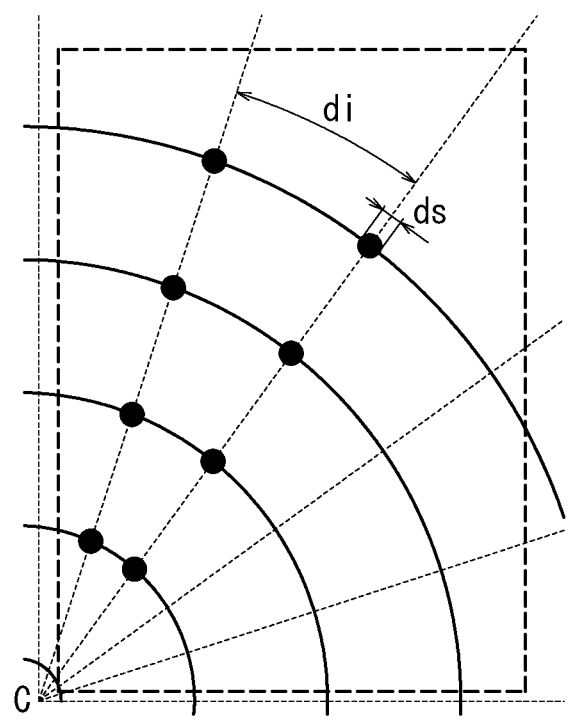
FIG. 8 is a diagram showing an example of the spiral scanning for sampling (in part) according the first embodiment.

FIG. 8 is a diagram showing an example of the spiral scanning for sampling according the first embodiment, which corresponds a part surrounded by the broken line in FIG. 7. The sampling time is made shorter at the outer periphery where the distance $r_c$ from the scanning center is large, so that the scanning distance per one sampling is maintained substantially close to a constant value within the scanning range on the object of observation 70. In particular, the sampling time t may preferably be adjusted so that the product with the scanning rate v can be maintained substantially at a constant value, the scanning distance $d_s$ can also be kept substantially constant, which is particularly preferred as it can eliminate variation in resolution. Here, when the distance is "maintained at substantially a constant value", it means that the distance varies in a range of, for example, about 30%.

Figure 9:
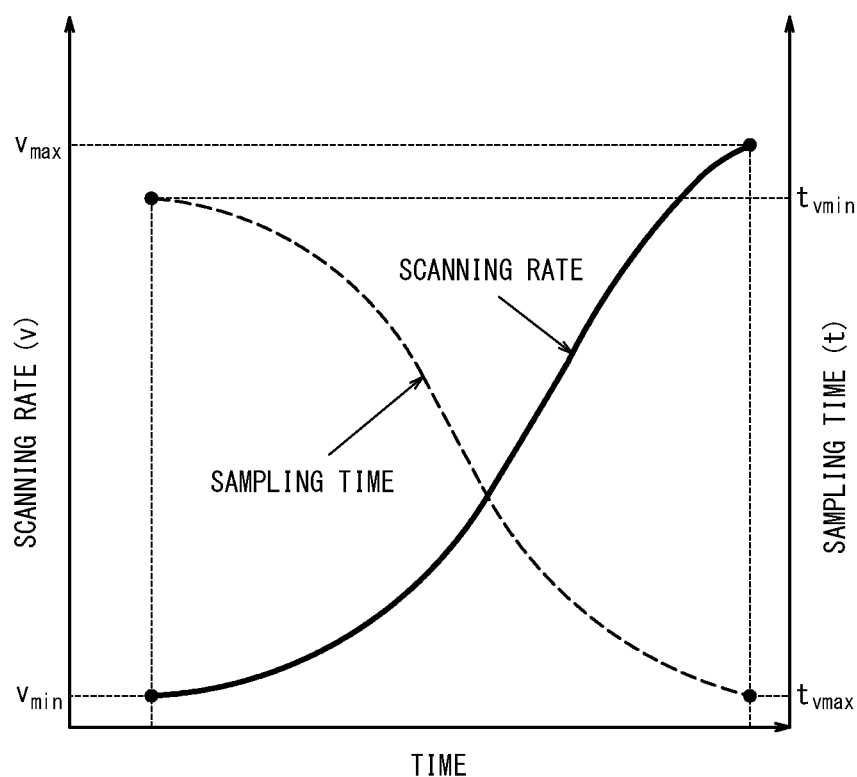
FIG. 9 is a graph showing an example of temporal change in scanning rate and sampling time.

FIG. 9 is a graph showing an example of temporal change in scanning rate and sampling time, in which the change in product (v×t) of the scanning rate and the sampling time is reduced to small. The scanning rate v takes a smallest value $v_{min}$ in the vicinity of the scanning center at the start of spiral scan, and takes a largest value $v_{max}$ in the outer periphery of the scanning range at the end of the scan. In contrast, the sampling time t reduces from the start of scan, or from the sampling time $t_{vmin}$ associated with the lowest scanning rate $v_{min}$, along with the progression of the scan, and takes a minimum value at the end of scan, or at the sampling time $t_{vmax}$ associated with the highest scanning rate $v_{max}$.

(Adjustment of Power of Laser Light)

Along with the change in sampling time, brightness at each sampling point (signal intensity that can be detected per one sampling) varies. In light thereof, it is preferred to change the power of laser light to be output from the light source unit 30 in accordance with changes in scanning rate v of the scanning part 23 scanning on the object of observation 70. The power of laser light is defined to satisfy the conditional expression (4), where $p_{vmin}$ and $p_{vmax}$ each represent the power of laser light obtained when the scanning rate v takes a minimum value and a maximum value, respectively, within a scanning range on the object of observation 70.

$$p_{vmin} \leq p_{vmax} \quad (4)$$

When $t_{vmax}$ is larger than $t_{vmin}$ as in the conditional expression (2), the sampling time becomes shorter at a position of the sampling point where the scanning rate becomes maximum, and thus the detection signal to be detected by the detection unit 40 is deteriorated in intensity, leading to a reduction in quantity of light per one pixel. The power of laser light may be adjusted so as to satisfy the conditional expression (4), to thereby reduce non-uniformity in brightness per one pixel at the maximum scanning rate relative to at least the brightness per one pixel at the minimum scanning rate, as compared with the case where the power of laser light to be emitted from the light source is kept constant.

Further, $p_{vmin}$ and $p_{vmax}$ may preferably satisfy the conditional expression (5) within the scanning range on the object of observation.

[Expression 7]

$$0.5 \leq \frac{p_{vmin}/v_{min}}{p_{vmax}/v_{max}} \leq 2 \quad (5)$$

Assuming that p represents the power of laser light, p/v represents the irradiation power of laser light per unit length in each sampling. As long as $p_{vmin}$ and $p_{vmax}$ fall within a range of satisfying the conditional expression (5), the range of change in quantity of light per unit length in sampling at the maximum scanning rate can be held within twice relative to at least the quantity of light at the minimum scanning rate. Meanwhile, when the range of change in irradiation power of laser light per unit length is reduced to 0.5 or less, the laser light irradiation power becomes excessively large in a region of high scanning rate, which may lead to biological damage when the object is a biological material. On the other hand, the range of change in irradiation power is increased to 2 or more, the brightness in a region of the highest scanning rate is reduced to half or less than that of the lowest scanning rate, which is not preferred.

Further, the conditional expression (10) may preferably be satisfied, where max(p/v) and min(p/v) each represent a maximum value and a minimum value, respectively, of a ratio of the power of laser light with respect to the scanning rate.

[Expression 8]

$$1 \leq \frac{\max(p/v)}{\min(p/v)} \leq 2 \quad (10)$$

When the conditional expression (10) is satisfied, the range of variation in p/v or the range of change in irradiation power of laser light per unit length can be held within twice across the entire spiral scanning range. In particular, the laser light power p may be adjusted so that the following expression can be obtained as substantially 1.

$$\frac{\max(p/v)}{\min(p/v)} \qquad \text{[Expression 9]}$$

Specifically, the laser light power p may be adjusted as proportional to the scanning rate v, so that the irradiation power of laser light per unit length during the scan for sampling can be maintained substantially constant. Here, a value of "substantially 1" refers to any value that varies in a range of, for example, about 30%.

Figure 10:
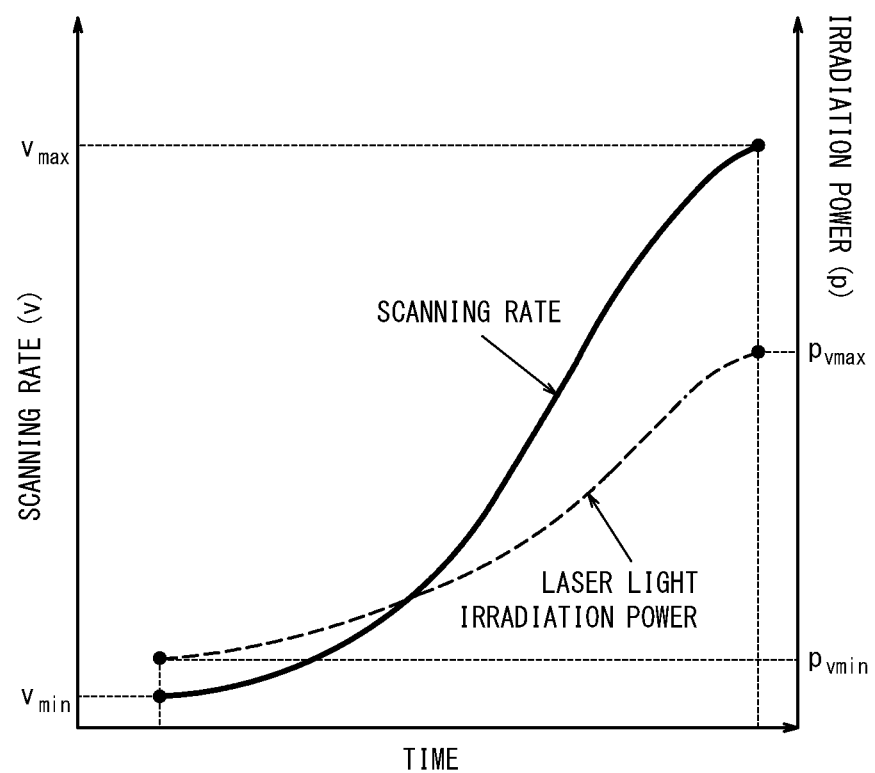
FIG. 10 is a graph showing an example of temporal change in scanning rate and laser light power output from the light source unit.

FIG. 10 is a graph showing an example of temporal change in scanning rate and irradiation power of laser light, in which the change in irradiation power of laser light per unit length is reduced to small. The laser light power p light increases from the start of scan, or from the laser light power $p_{vmin}$ associated with the lowest scanning rate $v_{min}$, along with the progression of the scan, and takes a maximum value at the end of scan, or at the laser light power $p_{vmax}$ associated with the highest scanning rate $v_{max}$.

(Adjustment of Detection Sensitivity)

Instead of adjusting the power of laser light as described above, the photodetectors 41R, 41G, 41B of the detection unit 40 each may be adjusted in detection sensitivity. The conditional expression (6) may be satisfied, where $s_{vmin}$ and $s_{vmax}$ each represent the detection sensitivity of the photodetectors the photodetectors 41R, 41G, 41B associated with the minimum and maximum values of the scanning rate v, respectively, within the scanning range on the object of observation 70.

$$s_{vmin} < s_{vmax} \qquad (6)$$

The conditional expression (6) may be adjusted so as to reduce non-uniformity between at least the detection signal intensity per one pixel at the minimum scanning rate and the detection signal intensity per one pixel at the maximum scanning rate, as compared with the case where the detection sensitivity of the detection unit 40 is kept constant.

Further, $s_{vmin}$ and $s_{vmax}$ may preferably satisfy the following conditional expression (7), within the scanning range on the object of observation.

[Expression 10]

$$0.5 \leq \frac{s_{vmin}/v_{min}}{s_{vmax}/v_{max}} \leq 2 \qquad (7)$$

Assuming that s represents the detection sensitivity of each of the photodetectors 41R, 41G, 41B of the detection unit 40, the detection sensitivity s can be varied to adjust the intensity of detection signal, in the same way of adjusting the intensity by varying the laser light power p. As long as $s_{vmin}$ and $s_{vmax}$ fall within a range satisfying the conditional expression (7), the range of change in detection signal per unit length of sampling at the maximum scanning rate can be held within twice of at least the detection signal at the minimum scanning rate. When the following expression takes a value of 0.5 or less, a highly-sensitive detector becomes necessary, which is inconvenient in terms of cost of the detector.

$$\frac{s_{vmin}/v_{min}}{s_{vmax}/v_{max}} \qquad \text{[Expression 11]}$$

Meanwhile, when the expression takes a value of 2 or more, there will be observed a pronounced decline in brightness in a region near the outer periphery of the scanning range, as in the case of the conditional expression (5).

Further, the following conditional expression (11) may preferably be satisfied, where max(s/v) and min(s/v) each represent the maximum value and the minimum value, respectively, of the detection sensitivity of the detection unit 40 with respect to the scanning rate within the scanning range on the object of observation 70.

[Expression 12]

$$1 \leq \frac{\max(s/v)}{\min(s/v)} \leq 2 \qquad (11)$$

In particular, the detection sensitivity s of each of the photodetectors 41R, 41G, 41B of the detection unit 40 may be adjusted such that the following expression can be obtained as substantially 1.

$$\frac{\max(s/v)}{\min(s/v)} \qquad \text{[Expression 13]}$$

Specifically, the detection sensitivity s may be adjusted as proportional to the scanning rate v, so that the detection signal during the scanning for sampling can be maintained substantially at a constant level. Here, a value of "substantially 1" refers to any value falling within a range of, for example, about 1 to 1.3.

(Adjustment of Sampling Interval)

When the scanning rate is varied while keeping the sampling interval constant, the distance between the center positions of the sampling points (hereinafter, referred to as sampling interval distance) is varied. The sampling interval distance can be expressed by the following expression.

$$r_c \times \omega \times t_s$$

Accordingly, the density of the sampling points increases as drawing closer to the scanning center, while the density decreases as approaching near the outer periphery of the scanning range (see FIG. 8). In such case, either one or both of the following inconveniences may be caused: the region with a lower scanning rate have a large number of sampling points per unit area, and thus, the sampling points are overlapped, which means that the samplings are performed wastefully; or the region with a higher scanning rate have a small number of sampling points per unit area, and thus, many of the pixels may not even have a single sampling point.

To avoid such inconveniences, according to the first embodiment, in addition to adjusting the sampling time as described above, the sampling interval may also be adjusted as described in below in accordance with changes in scanning rate on the object of observation 70.

The sampling interval may be varied so as to satisfy the conditional expression (8), where $t_{s\text{-}vmin}$ and $t_{s\text{-}vmax}$ each represent the sampling interval at a minimum value and a maximum value of the scanning rate, respectively, in the scanning range on the object of observation 70.

$$t_{s\text{-}vmax} < t_{s\text{-}vmin} \qquad (8)$$

In this manner, the degradation in resolution at the maximum scanning rate relative to at least the resolution at the minimum scanning rate can be reduced, as compared with the case where the sampling interval $t_s$ is kept constant.

Further, $t_{s\text{-}vmin}$ and $t_{s\text{-}vmax}$ may preferably be defined to satisfy the following conditional expression (12).

[Expression 14]

$$0.5 \le \frac{v_{max} \times t_{s\text{-}vmax}}{v_{min} \times t_{s\text{-}vmin}} \le 2 \qquad (12)$$

As long as $t_{s\text{-}vmin}$ and $t_{s\text{-}vmax}$ fall within a range of satisfying the conditional expression (12), the range of difference in sampling interval distance at the maximum scanning rate can be held within twice of at least the sampling interval distance at the minimum scanning rate. If the range of difference between the sampling interval distances is twice or more, the sampling points may overlap each other in the vicinity of the scanning center on the object of observation, or the number of sampling points is reduced to small in the outer periphery of the scanning range, leading to wasteful scanning and degradation in resolution.

Further, the following conditional expression (13) may preferably be satisfied, where v represents the scanning rate, $t_s$ represents the sampling interval, and max(v×$t_s$) and min (v×$t_s$) each represent a maximum value and a minimum value, respectively, of a product of the scanning rate and the sampling interval.

[Expression 15]

$$1 \le \frac{\max(v \times t_s)}{\min(v \times t_s)} \le 2 \qquad (13)$$

When the conditional expression (13) is satisfied, the range of the product v×$t_s$, or the range of variation in sampling interval difference, may be held within twice across the entire spiral scanning range, to thereby alleviate the variation in resolution in an image to be obtained.

Figure 11:
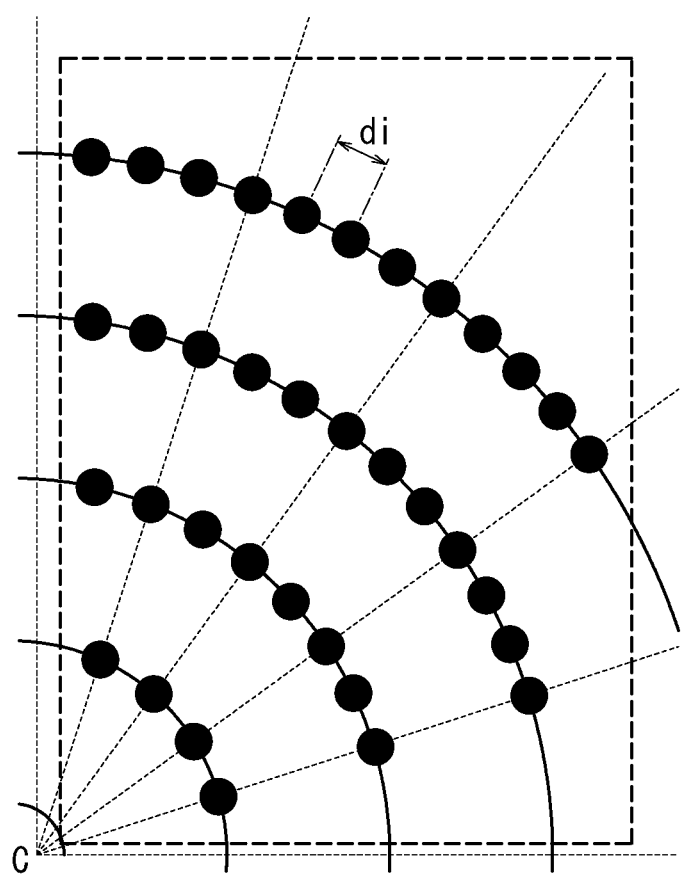
FIG. 11 is a diagram showing another example of the spiral scanning for sampling (in part) according the first embodiment.

FIG. 11 is a diagram showing another example of the spiral scanning for sampling (in part) according the first embodiment, which illustrates a case where the sampling interval is varied in addition to keeping the scanning distance substantially constant; the sampling interval is shorter in the outer periphery with increasing distance $r_c$ from the scanning center C. In particular, the sampling interval $t_s$ may preferably be adjusted such that the product with the scanning rate v can be maintained substantially at a constant value, which is particularly preferred as the sampling interval distance ($d_i$) can be kept substantially constant. Here, when the product is maintained substantially at constant value, it means that the product varies in a range of, for example, about 30%.

Figure 12:
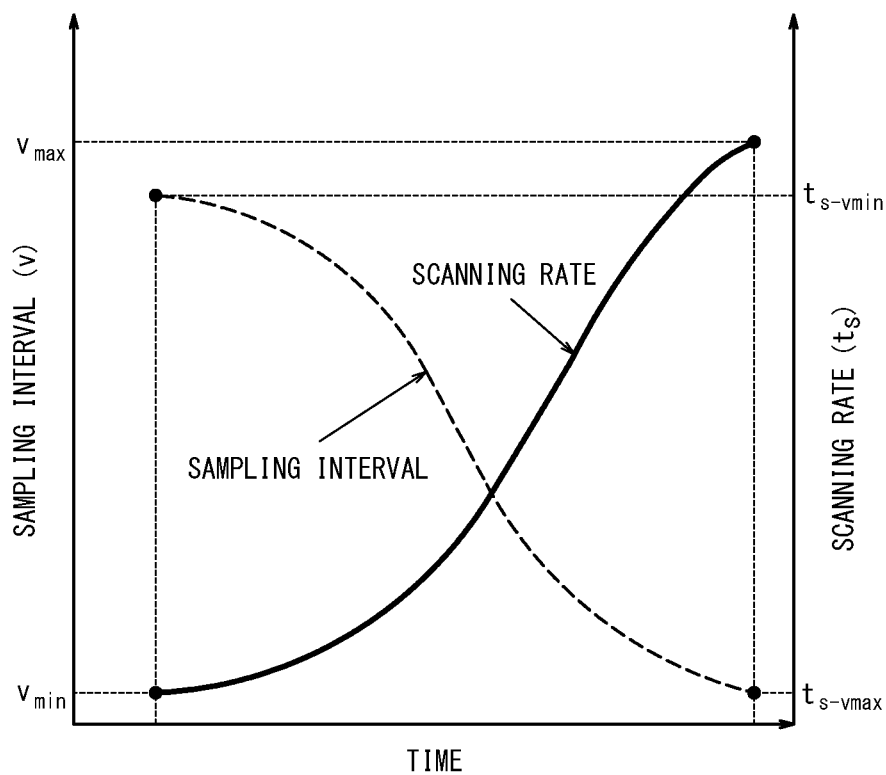
FIG. 12 is a graph showing an example of temporal change in scanning rate and sampling interval.

FIG. 12 is a graph showing an example of temporal change in scanning rate and sampling interval. The sampling interval $t_s$ reduces from the start of scan, that is, from the sampling interval $t_{s\text{-}vmin}$ associated with the lowest scanning rate $v_{min}$, along with the progression of the scan, and takes a minimum value at the end of scan, or at the sampling interval $t_{s\text{-}vmax}$ associated with the highest scanning rate $v_{max}$.

As described above, according to the first embodiment, the sampling time for detecting signal light per one sampling is configured to be varied in accordance with changes in scanning rate of the scanning part 23 on the object of observation 70, to thereby suppress variation in scanning distance resulting from variation in scanning rate. Therefore, it is possible to reduce degradation in resolution resulting from image blur ascribable to increased scanning distance.

Further, even when the sampling time is made shorter in accordance with changes in scanning rate in the vicinity of the outer periphery of the scanning range with higher scanning rate, the power of laser light from the light source unit 30 or the detection sensitivity of the detection unit 40 may be varied to be increased so as not to diminish the detection signal intensity of signal light to be detected by the detection unit 40, which can suppress weakening of signals detected in the vicinity of the outer periphery (the darkening of the image).

Further, the sampling interval can be made longer in accordance with changes in scanning rate in a region with a higher scanning rate, which can prevent sampling from being wastefully performed in the vicinity of the center with a lower scanning rate within the scanning range, or prevent the number of sampling points from excessively reduced in the vicinity of the outer periphery with a higher scanning rate within the scanning range. In particular, in the outer periphery with a higher scanning rate, the sampling time can be reduced to reduce the scanning distance, and thus, the sampling interval may be reduced so that the sampling points are arranged at the same density as in the center.

Further, the optical scanning endoscope apparatus 10 according to the first embodiment performed spiral scanning for sampling. In the spiral scanning, as compared with raster scanning, the scanning rate greatly varies between the vicinity of the center and the vicinity of the outer periphery of the scanning range, and thus, the resolution, the uniformity in brightness, and the sampling density within the scanning range greatly vary for each sampling. In contrast, in raster scanning, the difference in scanning rate can be reduced by not using the regions on the left and right ends. Therefore, the method of the present invention which involves varying the sampling time, the power of the laser light, and the sampling frequency is an effective solution in spiral scanning.

EXAMPLES

Example 1

An example of the optical scanning endoscope apparatus 10 according to the first embodiment is described in reference to specific parameters. In Example 1, the radius ($r_c$: distance from the scanning center C) of the spiral scanning range is defined as 200 µm, and the resonance frequency f is defined as 10 kHz (>30 fps×256 line=7.5 kHz). The sampling time t is defined based on the detection time of the detection unit 40, and t varies as proportional to 1/v. Similarly, the sampling frequency $t_s$ varies in proportional to 1/v. Further, the power of laser light is 3.2 E−10 [J/µm], which decreases as low as 1.6 E−10 [J/µm], along with the scanning toward the outer periphery. The detection sensitivity of the detection unit 40 is not adjusted during scanning for sampling.

TABLE 1

Parameter Values of Example 1

| Near the Scanning Center | | Near the Outer Periphery | |
|---|---|---|---|
| $r_c[\mu m]$ | 1.0E+00 | $r_c[\mu m]$ | 2.0E+02 |
| $f[Hz]$ | 1.0E+04 | $f[Hz]$ | 1.0E+04 |
| $\omega[Hz]$ | 6.3E+04 | $\omega[Hz]$ | 6.3E+04 |
| $v_{min}[\mu m/s]$ | 6.3E+04 | $v_{max}[\mu m/s]$ | 1.3E+07 |
| $t_{vmin}[s]$ | 1.6E−05 | $t_{vmax}[s]$ | 8.0E−08 |
| $t_{s-vmin}[s]$ | 1.6E−05 | $t_{s-vmax}[s]$ | 8.0E−08 |
| $p_{vmin}[W]$ | 2.0E−05 | $p_{vmax}[W]$ | 2.0E−03 |
| $v_{min} \times t_{vmin}[\mu m]$ | 1.0E+00 | $v_{max} \times t_{vmax}[\mu m]$ | 1.0E+00 |
| $v_{min} \times t_{s-vmin}[\mu m]$ | 1.0E+00 | $v_{max} \times t_{s-vmax}[\mu m]$ | 1.0E+00 |
| $p_{vmin}/v_{min}[J/\mu m]$ | 3.2E−10 | $p_{vmax}/v_{max}[J/\mu m]$ | 1.6E−10 |
| $\dfrac{v_{max} \times t_{vmax}}{v_{min} \times t_{vmin}}$ | | 1 | |
| $\dfrac{v_{max} \times t_{s-vmax}}{v_{min} \times t_{s-vmin}}$ | | 1 | |
| $\dfrac{p_{vmin}/v_{min}}{p_{vmax}/v_{max}}$ | | 2 | |

According to Example 1, the conditional expression (1) is satisfied, to thereby reduce degradation in resolution that would occur along with an increase in scanning rate from at least the minimum scanning rate to the maximum scanning rate, as compared with the case where the sampling time t is kept constant.

Further, the sampling time t varies in such a manner that the product with the scanning rate v can be constantly maintained to substantially 1 [µm], and thus the conditional expressions (2) and (3) can be satisfied. As a result, the scanning distance of each sampling is maintained substantially at a constant value, which can eliminate non-uniformity in resolution resulting from image blur ascribable to changes in scanning distance.

Further, the conditional expression (8) is satisfied, to thereby reduce degradation in resolution resulting from the increase in sampling interval distance from at least the sampling interval distance at the minimum scanning rate to the sampling interval distance at the maximum scanning rate, as compared with the case where the sampling interval $t_s$ is kept constant.

Further, the sampling interval $t_s$ varies in such a manner that the product with the scanning rate v can be constantly maintained to substantially 1 [µm], which also satisfies the conditional expressions (12) and (13). As a result, the sampling interval distance is kept substantially constant, to thereby reduce degradation in resolution resulting from unnecessary sampling in the vicinity of the scanning center and lowered density of sampling points in the vicinity of the outer periphery.

Further, the conditional expressions (4) and (5) are satisfied, to thereby suppress within a predetermined range non-uniformity in brightness per one pixel at the maximum scanning rate relative to at least the brightness per one pixel at the minimum scanning rate, as compared with the case where the power of laser light to be emitted from the light source is kept constant.

Here, according to Example 1, in order to obtain a constant product of the scanning rate v and the sampling time t, the photodetectors 41R, 41G, 41B of the detection unit 40 are each varied in detection time. However, the scanning rate v may alternatively be varied if the scanning rate v can supposedly be adjusted.

Second Embodiment

In the following, description is given of an optical scanning endoscope as another example of the optical scanning observation apparatus, according to a second embodiment. The optical scanning endoscope apparatus according to the second embodiment is different from the optical scanning endoscope apparatus according to the first embodiment in that the object of observation 70 is configured to be subjected to raster scanning, rather than spiral scanning. Therefore, the second embodiment is different from the first embodiment in terms of the configuration of the tip part 26 of the optical scanning endoscope (main body) 20. The second embodiment is further different in terms of the configuration of the light source unit 30.

Figure 13:
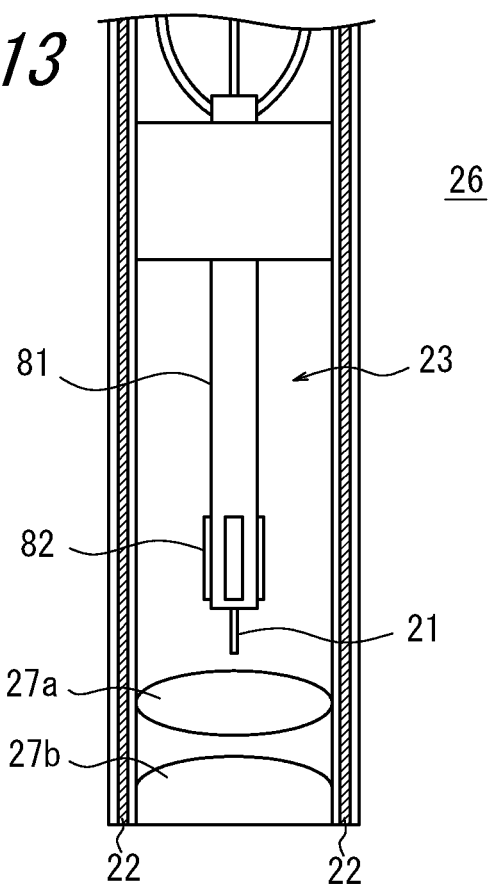
FIG. 13 is a sectional diagram of a tip part of an optical scanning endoscope (main body) of an optical scanning endoscope apparatus as an example of an optical scanning observation apparatus according to a second embodiment of the present invention.
Figure 14:
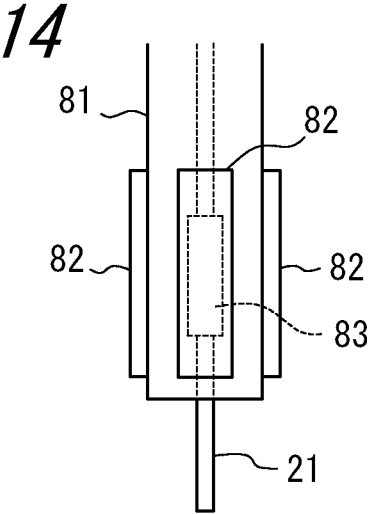
FIG. 14 is a diagram for illustrating a configuration of the scanning part of FIG. 13.

FIG. 13 is a sectional diagram of the tip part 26 of the optical scanning endoscope (main body) 20 of the optical scanning endoscope apparatus 10 of the second embodiment, and FIG. 14 is a diagram for illustrating a configuration of the scanning part 23 (scanning mechanism) of FIG. 13. The tip end of the SMF 21 is inserted through a cylindrical tube 81, so that the tip end protrudes from the cylindrical tube 23. On the outer periphery of the cylindrical tube 81, four electrodes 82 such as, for example, electromagnetic coils, are disposed equally spaced from one another in the circumferential direction. Further, magnets 83 are each disposed on the outer periphery of the SMF 21 at a position opposing to respective one of the electrodes 82. The electrodes 82 and the magnets 83 are each formed in a pair, and two pairs of the electrodes 82 and the magnets 83 form an oscillation mechanism, so as to oscillate the SMF 21 by an electromagnetic force in mutually-orthogonal directions (hereinafter, each referred to as X direction and Y direction, respectively).

Figure 15:
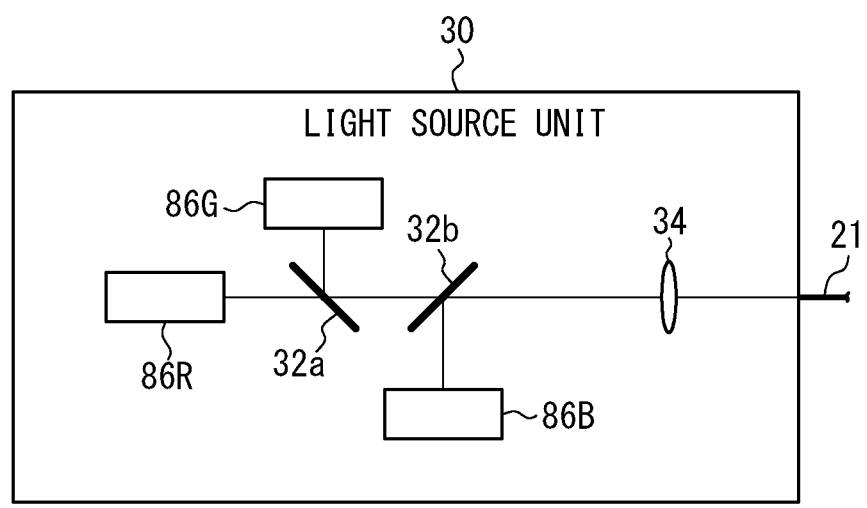
FIG. 15 is a diagram illustrating a schematic configuration of a light source unit of the optical scanning endoscope apparatus according to the second embodiment.

FIG. 15 is a diagram illustrating a schematic configuration of the light source unit 30 of the optical scanning endoscope apparatus 10 according to the second embodiment. In the second embodiment, a laser source 86R for red and a laser source 86B for blue each employ a LD source, and a laser source 86G for green employs a DPSS laser. Unlike the first embodiment, the light source unit 30 is not provided with the AOM 33. However, laser diodes or semiconductor lasers constituting the laser sources 86R, 86G, 86B can be directly modulated, to thereby adjust the laser light irradiation time per one sampling. Alternatively, an acousto-optic tunable filter (AOTF) may be provided between the dichroic mirror 32b and the lens 34, to thereby adjust the laser light irradiation time.

The rest of the configuration is similar to that of the first embodiment, and thus, the same components are denoted by the same reference numerals and the description thereof is omitted.

Next, description is given of the operation of the optical scanning endoscope apparatus 10 according to the second embodiment. The scanning part 23 oscillates the tip end of the SMF 21 in the X direction at a resonance frequency $f_X$. The scanning part 23 also oscillates the SMF 21 in the Y direction at a frequency $f_Y$ smaller than $f_X$. In this manner, laser light irradiated onto the object of observation 70 is sequentially raster-scanned correspondingly to the oscillation of the SMF 21, and thus, signal light to be obtained from the raster-scanned laser light may be detected and processed, to thereby generate a two-dimensional image.

Figure 16:
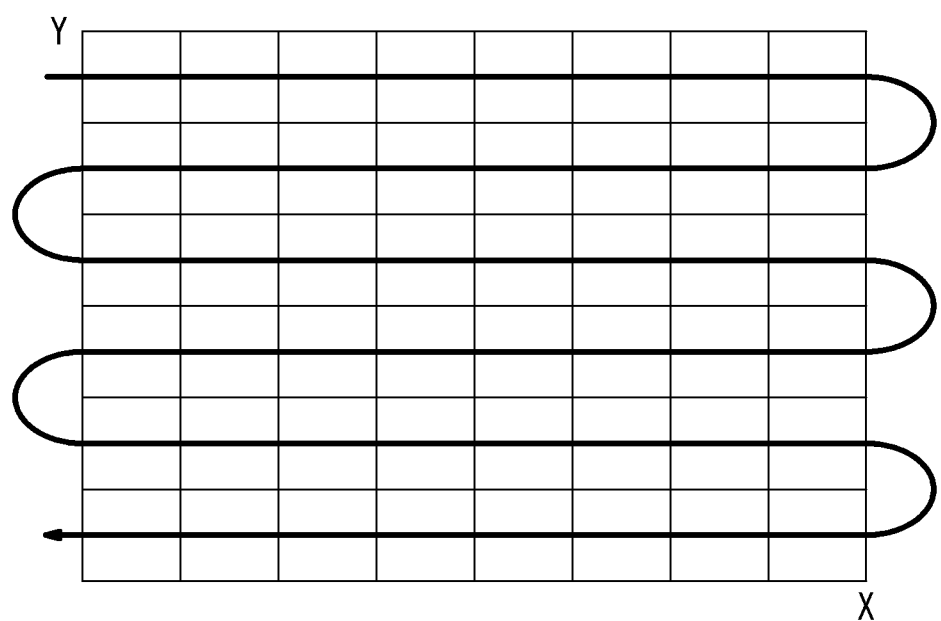
FIG. 16 is a diagram illustrating a sampling path of raster scanning.
Figure 17:
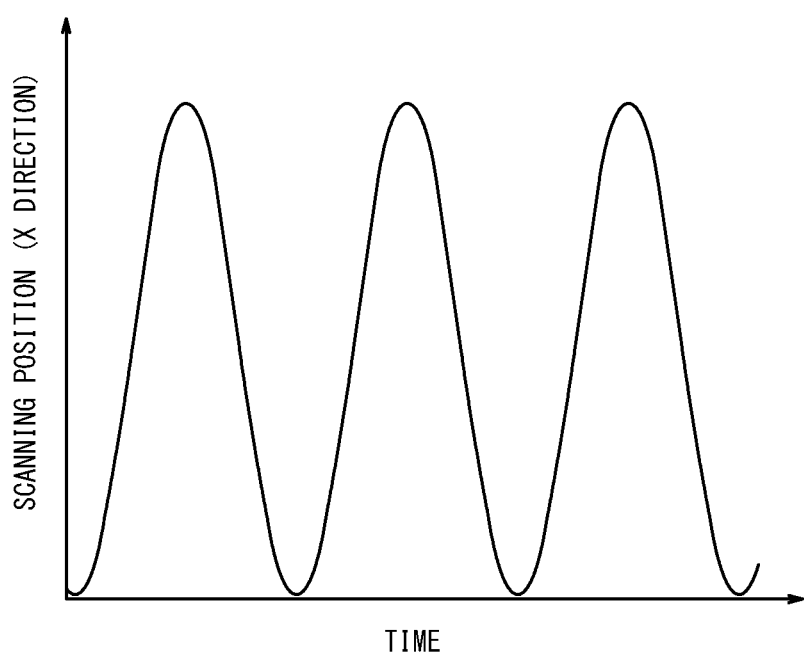
FIG. 17 is a graph showing an example of temporal change in scanning position in one direction in raster scanning on an object of observation.
Figure 18:
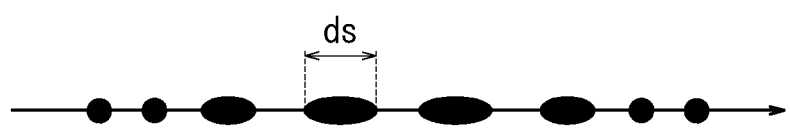
FIG. 18 is a diagram illustrating an example of sampling on a raster line according to a conventional example.

FIG. 16 is a diagram illustrating a sampling path of raster scanning, and FIG. 17 is a graph showing an example of temporal change in scanning position in the X direction in raster scanning on the object of observation 70. The emitting end of the SMF 21 is oscillated in the X direction at the resonance frequency $f_x$, while the scanning position is sinusoidally displaced with time. In this case, within the scanning range on the object of observation 70, the scanning rate is lower on both ends of the scan in the X direction while the scanning rate is higher in the vicinity of the center of the scan. Here, the distance to be scanned can be expressed as v×t, where v represents the scanning rate and t represents the sampling time. FIG. 18 illustrates changes in the scanning distance $d_s$ per one sampling, with the sampling time t for scanning in the X-direction being kept constant. In this case, the rasters become longer in scanning distance per one sampling around the center of the scan in the X direction, which leads to a fear that an image blur be generated and the resolution be degraded.

Figure 19:
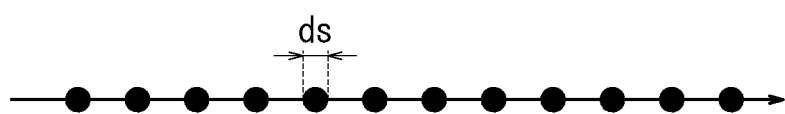
FIG. 19 is a diagram illustrating an example of the sampling on a raster line according to the second embodiment.

In light thereof, according to the second embodiment, the laser light irradiation time of the light source unit 30 is adjusted so as to reduce the sampling time per one sampling in the center region with a higher scanning rate, to thereby reduce degradation in resolution resulting from image blur ascribable to increased scanning distance. Even in the second embodiment, the sampling time t may also be controlled so as to satisfy the conditional expressions (1) to (3), so as to obtain effect similar to that of the first embodiment. Here, the sampling time t represents laser light irradiation time per one sampling. In particular, the product of the scanning rate and the sampling time may be maintained substantially at a constant value, to thereby keep the scanning distance $d_s$ substantially constant along the scanning range on the object of observation 70, as illustrated in FIG. 19.

Further, as in the first embodiment, the laser light power p, the detection sensitivity s of each of the photodetectors 41R, 41G, 41B, and the sampling interval $t_s$ may be adjusted so as to satisfy the conditional expressions (4) to (8), (10) to (13) as appropriate, in addition to varying the sampling time t in accordance with the scanning rate v, a similar effect as in the first embodiment can be obtained for each conditional expression. FIG. 19 above illustrates an example where the sampling interval has also been adjusted in addition to adjusting the sampling time.

Example 2

An example of the optical scanning endoscope apparatus 10 according to the second embodiment is described in reference to specific parameters. In Example 2, an amplitude $r_x$ in the X direction (distance from the amplitude center) of the raster scanning range is defined as 200 μm, and the resonance frequency ($f_x$) is defined as 10 kHz (>30 fps×256 line=7.5 KHz). The average scanning rate $v_x$ in the X direction is 8.0 E+6 μm/s. The laser light power is defined in consideration of biological damage to the object of observation 70.

TABLE 2

| Parameter Values of Example 2 | | | |
|---|---|---|---|
| Near the Scanning Center | | Near the Periphery | |
| $r_x$[μm] | 1.0E+00 | $r_x$[μm] | 2.0E+02 |
| $f_x$[Hz] | 1.0E+04 | $f_x$[Hz] | 1.0E+04 |
| $f_y$[Hz] | 3.0E+01 | fy[Hz] | 3.0E+01 |

TABLE 2-continued

| Parameter Values of Example 2 | | | |
|---|---|---|---|
| Near the Scanning Center | | Near the Periphery | |
| $v_{max}$[μm/s] | 3.2E+07 | $v_{min}$[μm/s] | 2.0E+06 |
| $t_{vmax}$[s] | 3.1E−08 | $t_{vmin}$[s] | 5.0E−07 |
| $t_{s-vmax}$[s] | 3.1E−08 | $t_{s-vmin}$[s] | 5.0E−07 |
| $p_{vmax}$[W] | 2.0E−03 | $p_{vmin}$[W] | 1.3E−04 |
| $v_{max} \times t_{vmax}$[μm] | 1.0E+00 | $v_{min} \times t_{vmin}$[μm] | 1.0E+00 |
| $v_{max} \times t_{s-vmax}$[μm] | 1.0E+00 | $v_{min} \times t_{s-vmin}$[μm] | 1.0E+00 |
| $p_{vmax}/v_{max}$[J/μm] | 6.3E−11 | $p_{vmin}/v_{min}$[J/μm] | 6.3E−11 |
| $\dfrac{v_{max} \times t_{vmax}}{v_{min} \times t_{vmin}}$ | | 1 | |
| $\dfrac{v_{max} \times t_{s-vmax}}{v_{min} \times t_{s-vmin}}$ | | 1 | |
| $\dfrac{p_{vmin}/v_{min}}{p_{vmax}/v_{max}}$ | | 1 | |

According to Example 2, the conditional expressions (1) and (2) are satisfied, to thereby reduce degradation in resolution resulting from image blur ascribable to increased scanning distance at a maximum scanning rate relative to at least the resolution at a minimum scanning rate.

Further, the conditional expressions (8) and (12) are satisfied, to thereby reduce degradation in resolution resulting from lowered density of sampling points at a maximum scanning rate relative to at least the density of sampling points at a minimum scanning rate.

Further, the conditional expressions (4) and (5) are satisfied, to thereby suppress within a predetermined range non-uniformity in brightness per one pixel at a maximum scanning rate relative to at least the brightness per one pixel at a minimum scanning rate, as compared with the case where the power of laser light to be emitted from the light source is kept constant.

In addition to the above, the sampling time t, the sampling interval $t_s$, and the laser light power p may be adjusted so as to maintain the product of the scanning rate and the sampling time (v×t), the product of the scanning rate and the sampling interval (v×$t_s$), and the ratio of the laser light power to the scanning rate (p/v) each substantially at a constant value across the scanning range on the object of observation 70, so that the scanning distance per each sampling, the sampling interval distance, and the brightness per one pixel can be made uniform.

Third Embodiment

FIG. 20 is a block diagram illustrating a schematic configuration of a laser scanning microscope apparatus 110 as an example of an optical scanning observation apparatus, according to a third embodiment of the present invention. The laser scanning microscope apparatus 110 is configured by including: a laser scanning microscope (main body) 120; a light source unit 130 (light source); a detection unit 140 (detector); a computer 150; and a display device 160. The light source unit 130 and the laser scanning microscope (main body) are optically connected to each other via a SMF 121. The detection unit 140 and the laser scanning microscope (main body) 120 may be housed in casings that are directly coupled to each other, or may be housed in the same casing. Further, the computer 150 is electrically connected to the laser scanning microscope (main body) 120, the light source unit 130, the detection unit 140, and the display device 160.

The light source unit 130 includes: LD (semiconductor lasers) 131R, 131G, 131B for red, green, and blue; dichroic mirrors 132a, 132b; a AOTF 133; and a lens 134. The arrangement of the LDs 131R, 131G, 131B, and the optical characteristics and arrangement of the dichroic mirrors 132a, 132b are similar to those of the first embodiment, and thus the description thereof is omitted. The AOTF 133 is an optical element capable of selecting wavelength and modulating intensity of laser light obtained by multiplexing laser lights from the LDs 131R, 131G, 131B, and switches at high speed between laser light of each color of red, blue, and green, for irradiation at each sampling point. The AOTF 133 is controlled by the light source controller (not shown) of the computer 150. Laser light having passed through the AOTF 133 is caused to incident on the incident end of the SMF 121 through the lens 134.

The laser scanning microscope (main body) 120 includes: a lens 122; a dichroic mirror 123; a galvanometer scanner 124 (scanning mechanism); a mirror 125; a pupil projection lens 126; an imaging lens 127; and an objective lens 128. Here, the galvanometer scanner 124 is disposed at a position conjugate to the pupil position of the objective lens 128.

The lens 122 is a lens for collimating a laser beam emitted from the emitting end of the SMF 121. The dichroic mirror 123 has optical characteristics for transmitting laser light incident from the light source unit 130 and reflecting fluorescence light generated from an object of observation 170 irradiated with laser light. The galvanometer scanner 124 includes galvano mirrors 124a and 124b, so as to deflect, in mutually-orthogonal biaxial directions (referred to as X direction and Y direction), laser light that has been emitted from the SMF 121 and passed through the dichroic mirror 123.

The laser light that has been deflected by the galvano mirrors 124a, 124b is reflected by the mirror 125 and passes through the pupil projection lens 126, the imaging lens 127, and the objective lens 128 with, for example, a magnifying power of 25, so as to be condensed on the object of observation 170 to form a spot. Along therewith, the galvanometer scanner 124 is driven to scan the spot thus formed on the object of observation 170.

The object of observation 170 is applied with dyes of three colors which are to be excited by laser lights of three colors of red, blue, and green each emitted from the LDs 131R, 131G, and 131B, respectively, of the light source unit 130, so as to generate fluorescence lights of different wavelengths. The object of observation 170 scanned with laser light generates fluorescence lights, which inversely travel along an optical path along which the laser light has been propagated and are separated by the dichroic mirror 123 before being incident on the detection unit 140.

The detection unit 140 includes: PMTs (photomultiplier tubes) 141R, 141G, 141B for detecting each fluorescence light generated by laser lights of three colors emitted from the LDs 131R, 131G, 131B; and dichroic mirrors 142a, 142b. As in the first embodiment, the two dichroic mirrors 142a and 142b separate three fluorescence lights having different wavelengths, so as to cause each light to be incident on the corresponding one of the PMTs 141R, 141G, 141B, respectively. The multiplication factors of the PMTs 141R, 141G, 141B are each controlled by the detection controller (not shown) of the computer 150. Further, output signals from the PMTs 141R, 141G, 141B are transmitted to a signal processor (not shown) of the computer 150, where an image of the object of observation 170 is generated to be displayed on the display device 160.

Here, the computer 150 includes, similarly to the computer 50 of the first embodiment: the light source controller; the detection controller; the scanning controller; the signal processor; the memory; and the input part, and carries out the same processing as the first embodiment except in that the computer 150 carries out control adapted to raster scanning, and thus the detailed description thereof is omitted.

The laser scanning microscope apparatus 110 according to the third embodiment configured as described above can be operated as follows.

The laser scanning microscope apparatus 110 sequentially scans, by the galvanometer scanner 124, the object of observation 170 with laser light output from the light source unit 130. Here, the galvanometer scanner 124 oscillates the laser light at a resonance frequency $f_X$ of the galvano mirror 124a in the X direction in a plane perpendicular to the optical axis of the objective lens 128, while oscillating the laser light, by the galvano mirror 124b, at a frequency $f_Y$ in the Y direction. At this time, the oscillation at the resonance frequency in the X direction is substantially a sinusoidal oscillation.

The distance scanned per one sampling is expressed as:

$$v \times t,$$

where v represents the scanning rate, and t represents the sampling time. The sampling time is defined by one or both of the detection time taken by the PMTs 141R, 141G, 141B, and the laser light irradiation time controlled by the AOTF 133.

The galvanometer scanner 124 produces a sinusoidal scan in the X direction, and thus, the scanning rate becomes higher as being closer to the center in the X direction within the scanning range of the object of observation 170. Therefore, as in the optical scanning endoscope of the second embodiment, the sampling time t per one sampling is made shorter in the center region with a higher scanning rate, to thereby reduce degradation in resolution resulting from image blur ascribable to increased scanning distance. Meanwhile, in the periphery of the scanning range, the resolution is degraded due to aberration in the optical system. In light thereof, the sampling time t may further be reduced in the vicinities of both ends in the Y direction, to thereby reduce degradation in resolution. Even in the third embodiment, the sampling time t may be controlled to satisfy the conditional expressions (1) to (3), so as to obtain operation and effect similar to those of the first embodiment. The sampling time t refers to time it takes for laser lights of respective colors to transmit through the AOTF 133.

Further, the cycle period of the light-transmitting state and the light-shielding state of the AOTF 133 with respect to laser lights of respective colors may be varied, so as to vary the sampling interval $t_s$ in accordance with changes in scanning rate, with the result that the density of the sampling points can be brought close to a more uniform state.

Further, as in the first and second embodiments, the laser light power p from the light source unit 130 or the detection sensitivity s of the detection unit 140 may be adjusted, to thereby make uniform the intensity of detection signals. In particular, according to the third embodiment, PMTs are used in the detection unit 140, which allows for varying image magnification in a wide range. With this configuration, non-uniformity in brightness per each pixel can be suppressed.

Therefore, as in the first embodiment, in addition to varying the sampling time t in accordance with the scanning rate v, the conditional expressions (4) to (8), and (10) to (13)

may be satisfied as appropriate, to thereby obtain, for each conditional expression, an effect similar to that of the first embodiment.

As described above, according to the third embodiment, the sampling time for detecting signal light per one sampling is varied in accordance with changes in scanning rate of the galvanometer scanner 124 scanning on the object of observation 170, to thereby suppress variation in scanning distance resulting from variation in scanning rate. Therefore, it is possible to reduce degradation in resolution resulting from image blur ascribable to increased scanning distance.

Further, the detection intensity of the detection unit 140 can be varied to be increased, so as not to diminish the signal intensity of signal light to be detected by the detection unit 140 even in a case where the sampling time is made shorter in a region with a higher scanning rate, namely, at the center in the X direction within the scanning range, to thereby suppress weakening of signals detected in the center in the X direction (darkening of the image). In particular, PMTs are used in the detection unit 140, which allows the detection sensitivity to be adjusted in a wide range.

Further, the sampling interval can be varied to be increased in a region with a higher scanning rate, along with changes in scanning rate, to thereby prevent sampling from being wastefully performed at both ends in the X direction with a lower scanning rate or prevent the number of sampling points from excessively reduced in the center in the X direction with a higher scanning rate.

In the third embodiment, the amplitude of the galvanometer scanner 124 is sinusoidally varied relative to time. However, the amplitude may be varied in a more complicated manner. In such case, the scanning rate at each sampling point may be measured in advance using, for example, a PSD (position sensitive detector), or there may be provided tilt sensors for detecting in real time the layout angles of the galvano mirrors 124a and 124b of the galvanometer scanner so as to transmit, by the sensors, angular signals in real time to the computer 150, so that the angular signals may be used for controlling each components and for generating an image.

Example 3

An example of the laser scanning endoscope apparatus 110 according to the third embodiment is described in reference to specific parameters. An objective lens with a magnifying power of 25 is used as the objective lens 128, and the amplitude $r_x$ in the X direction (distance from the amplitude center) on the sample surface is defined as 280 μm and the resonance frequency ($f_x$) is defined as 10 kHz. The average scanning rate $v_x$ in the X direction is 11.2 E+6 μm/s. The laser light power is defined in consideration of biological damage to the object of observation 170.

TABLE 3

| Parameter Values of Example 3 | | | |
|---|---|---|---|
| Near the Scanning Center | | Near the Periphery | |
| $r_X$[μm] | 1.0E+00 | $r_X$[μm] | 2.8E+02 |
| $f_X$[Hz] | 1.0E+04 | $f_X$[Hz] | 1.0E+04 |
| $f_Y$[Hz] | 3.0E+01 | $f_Y$[Hz] | 3.0E+01 |
| $v_{max}$[μm/s] | 2.2E+07 | $v_{min}$[μm/s] | 5.5E+06 |
| $t_{vmax}$[s] | 4.5E−08 | $t_{vmin}$[s] | 1.5E−07 |
| $t_{s-vmax}$[s] | 4.5E−08 | $t_{s-vmin}$[s] | 1.8E−07 |
| $s_{vmax}$[V] | 7.0E+02 | $s_{vmin}$[W] | 1.8E+02 |
| $v_{max} \times t_{vmax}$[μm] | 1.0E+00 | $v_{min} \times t_{vmin}$[μm] | 8.3E−01 |

TABLE 3-continued

| Parameter Values of Example 3 | | | |
|---|---|---|---|
| Near the Scanning Center | | Near the Periphery | |
| $v_{max} \times t_{s-vmax}$[μm] | 1.0E+00 | $v_{min} \times t_{s-vmin}$[μm] | 1.0E+00 |
| $s_{vmax}/v_{max}$[V·s/μm] | 3.2E−10 | $s_{vmin}/v_{min}$[V·s/μm] | 3.2E−05 |
| $\dfrac{v_{max} \times t_{vmax}}{v_{min} \times t_{vmin}}$ | | 0.83 | |
| $\dfrac{v_{max} \times t_{s-vmax}}{v_{min} \times t_{s-vmin}}$ | | 1 | |
| $\dfrac{s_{vmin}/v_{min}}{s_{vmax}/v_{max}}$ | | 1 | |

According to Example 3, the conditional expressions (1) and (2) are satisfied, to thereby suppress with in a predetermined range the degradation in resolution resulting from image blur ascribable to increased scanning distance at a maximum scanning rate relative to at least the resolution at a minimum scanning rate.

Further, the conditional expressions (8) and (12) are satisfied, to thereby reduce degradation in resolution resulting from the difference in density between at least the sampling points at a minimum scanning rate and the sampling points at a maximum scanning rate, as compared with a case where the sampling interval is kept constant.

Further, the conditional expressions (6) and (7) are satisfied, to thereby suppress within a predetermined range non-uniformity in brightness (intensity of detection signal) per one pixel at a maximum scanning rate relative to at least the brightness per one pixel at a minimum scanning rate, as compared with the case where the detection sensitivity of each of the PMTs 141R, 141G, 141B of the detection unit 40 is kept constant.

It should be noted that the present invention is not limited only to the aforementioned embodiments, and may be subjected to various modifications and alterations. For example, the scanning for sampling is not limited to spiral sampling or raster sampling. An effect similar to those of the first to third embodiments may also be obtained in, for example, Lissajour scanning.

Further, in each of the aforementioned embodiments, the light source unit emits laser light of each color of red, green, and blue. However, the colors of lasers included in the light source unit are not limited the combination of these three colors, and lasers of different wavelengths and numbers may be used. In addition, the optical characteristics and arrangement of the dichroic mirrors for multiplexing laser lights may be determined as appropriate depending on the laser source to be used.

Further, in the first and second embodiments, the computer, the light source unit, the detection unit, and the optical scanning endoscope (main body) are not necessarily configured independently of one another, and may be combined in various ways. For example, the computer, the light source unit, and the detection unit may be housed in one casing. The same applies to the third embodiment.

In the third embodiment, part of the optical system for irradiating laser light is shared with part of the optical system for detecting fluorescence light, which may also be configured without being shared with each other. Further, the optical scanning observation apparatus of the present invention may also be configured to irradiate an object of observation with laser light from a light source so as to detect light that has been transmitted through the object.

REFERENCE SIGNS LIST 10 optical scanning endoscope apparatus
20 optical scanning endoscope
21 SMF (single mode fiber)
22 MMF (multi mode fiber)
23 scanning part
23a piezoelectric element
24 operation part
25 insertion part
26 tip part
27a, 27b lens
30 light source unit
31R, 31B LD (laser diode)
31G DPSS laser (semiconductor-pumped solid state laser)
32a, 32b dichroic mirror
33 AOM (acousto-optic modulator)
34 lens
40 detection unit
41R, 41G, 41B photodetector
42a, 42b dichroic mirror
43 lens
50 computer
51 light source controller
52 detection controller
53 scanning controller
54 signal processor
55 controller
56 memory
60 display device
70 object of observation
81 cylindrical tube
82 electrode
83 magnet
86R, 86B LD (laser diode)
86G DPSS laser (semiconductor-pumped solid state laser)
110 laser scanning microscope apparatus
120 laser scanning microscope (main body)
121 SMF (single mode fiber)
122 lens
123 DM (dichroic mirror)
124 galvanometer scanner
124a, 124b galvano mirror
125 mirror
126 pupil projection lens
127 imaging lens
128 objective lens
130 light source unit
131R, 131G, 131B LD (laser diode)
132a, 132b dichroic mirror
133 AOTF (acousto-optic tunable filter)
134 lens
140 detection unit
141R, 141G, 141B PMT (photomultiplier tube)
142a, 142b DM (dichroic mirror)
150 computer
160 display device

The invention claimed is:

1. An optical scanning observation apparatus, comprising:
a light source configured to output laser light;
a scanning mechanism configured to scan, on an object of observation, a condensing position of the laser light;
a detector configured to detect signal light obtained through the scanning of the laser light within a time frame of a detection time, and convert the signal light that is detected into an electric signal; and
a processor configured to define a sampling time per one sampling of the signal light by controlling the light source to perform a change in an irradiation time of the laser light within the time frame of the detection time, the irradiation time of the laser light being changed in accordance with a change in a scanning rate of scanning the condensing position of the laser light by the scanning mechanism.

2. The optical scanning observation apparatus according to claim 1,
wherein the processor is configured to define the sampling time per one sampling within a scanning range on the object of observation such that:
where a minimum value of the scanning rate is represented as $v_{min}$;
where a maximum value of the scanning rate is represented as $v_{max}$;
where a sampling time per one sampling at $v_{min}$ is represented as $t_{vmin}$; and
where a sampling time per one sampling at $v_{max}$ is represented as $t_{vmax}$,
$t_{vmin}$ and $t_{vmax}$ satisfy a conditional expression (1):

$$t_{vmin} > t_{vmax} \qquad (1).$$

3. The optical scanning observation apparatus according to claim 2,
wherein the processor is configured to define the sampling time per one sampling such that $t_{vmin}$ and the $t_{vmax}$ satisfy a conditional expression (2):

$$0.5 \leq \frac{v_{max} \times t_{vmax}}{v_{min} \times t_{vmin}} \leq 2. \qquad (2)$$

4. The optical scanning observation apparatus according to claim 1,
wherein the processor is configured to define the sampling time per one sampling such that within a scanning range on the object of observation:
where the scanning rate is represented as v;
where the sampling time per one sampling is represented as t; and
wherein the product of v and t has a maximum value represented as max(v×t) and a minimum value represented as min(v×t), max(v×t) and min(v×t) satisfying a conditional expression (3):

$$1 \leq \frac{\max(v \times t)}{\min(v \times t)} \leq 2. \qquad (3)$$

5. The optical scanning observation apparatus according to claim 1,
wherein, within a scanning range on the object of observation, the processor is configured to vary the sampling time such that the product of the sampling time and the scanning rate is maintained substantially at a constant value.

6. The optical scanning observation apparatus according to claim 1,
wherein the processor is configured to define the sampling time per one sampling by controlling the detector to perform a change in a detection time of the detector per one sampling in accordance with the change in the scanning rate of scanning the condensing position of the laser light by the scanning mechanism.

7. The optical scanning observation apparatus according to claim 1,
wherein the processor is configured to control the light source to vary a power of the laser light in accordance with the change in the scanning rate of scanning the condensing position of the laser light by the scanning mechanism.

8. The optical scanning observation apparatus according to claim 7,
wherein, within a scanning range on the object of observation, the processor is configured to control the light source to vary the power of the laser light, such that:
where a minimum value of the scanning rate is represented $v_{min}$;
where a maximum value of the scanning rate is represented as $v_{max}$;
where the power of the laser light at $v_{min}$ is represented as $p_{vmin}$; and
where the power of the laser light at $v_{max}$ is represented as $p_{vmax}$,
$p_{vmin}$ and $p_{vmax}$ satisfy a conditional expression (4):

$$p_{vmin} < p_{vmax} \qquad (4).$$

9. The optical scanning observation apparatus according to claim 8,
wherein the processor is configured to control the light source, within the scanning range on the object of observation, to vary the power of the laser light such that $p_{vmin}$ and the $p_{vmax}$ satisfy a conditional expression (5):

$$0.5 \leq \frac{p_{vmin}/v_{min}}{p_{vmax}/v_{max}} \leq 2. \qquad (5)$$

10. The optical scanning observation apparatus according to claim 1,
wherein the processor is configured to control the detector to vary a detection sensitivity for detecting the signal light, in accordance with the change in the scanning rate of scanning the condensing position of the laser light by the scanning mechanism.

11. The optical scanning observation apparatus according to claim 10,
wherein the processor is configured to control the detector, within a scanning range on the object of observation, to vary the detection sensitivity such that:
where a minimum value of the scanning rate is represented as $v_{min}$;
where a maximum value of the scanning rate is represented as $v_{max}$;
where a detection sensitivity at $v_{min}$ is represented as $s_{vmin}$; and
where a detection sensitivity at $v_{max}$ is represented as $s_{vmax}$,
$s_{vmin}$ and the $s_{vmax}$ satisfy a conditional expression (6):

$$s_{vmin} < s_{vmax} \qquad (6).$$

12. The optical scanning observation apparatus according to claim 11,
wherein the processor is configured to control the detector, within the scanning range on the object of observation, to vary the detection sensitivity such that $s_{vmin}$ and the $s_{vmax}$ satisfy a conditional expression (7):

$$0.5 \leq \frac{s_{min}/v_{min}}{s_{max}/v_{max}} \leq 2. \qquad (7)$$

13. The optical scanning observation apparatus according to claim 1,
wherein the processor is configured to control one or more of the light source, the scanning mechanism and the detector to vary a sampling interval between two samplings in accordance with the change in the scanning rate of scanning the condensing position of the laser light of the scanning mechanism.

14. The optical scanning observation apparatus according to claim 13,
wherein the processor is configured to control one or more of the light source, the scanning mechanism and the detector to vary the sampling interval between two samplings, within a scanning range on the object of observation, such that:
where a sampling interval at a minimum value of the scanning rate is represented as $t_{s-vmin}$; and
where a sampling interval at a maximum value of the scanning rate is represented as $t_{s-vmax}$,
$t_{s-vmin}$ and the $t_{s-vmax}$ satisfying a conditional expression (8):

$$t_{s-vmax} < t_{s-vmin} \qquad (8)$$

15. The optical scanning observation apparatus according to claim 1,
wherein the processor is configured to control the scanning mechanism to spirally scan, on the object of observation, the condensing position of the laser light.

16. A method of controlling an optical scanning observation apparatus, wherein the optical scanning observation apparatus comprises:
a light source configured to output laser light;
a scanning mechanism configured to scan, on an object of observation, a condensing position of the laser light; and
a detector configured to detect signal light obtained through the scanning of the laser light within a time frame of a detection time, and convert the signal light that is detected into an electric signal, and
wherein the method comprises defining a sampling time per one sampling of the signal light by controlling the light source to perform a change in an irradiation time of the laser light within the time frame of the detection time, the irradiation time of the laser light being changed in accordance with a change in a scanning rate of scanning the condensing position of the laser light by the scanning mechanism.

17. A computer-readable storage device storing instructions for controlling an optical scanning observation apparatus,
wherein the optical scanning observation apparatus comprises:
a light source configured to output laser light;
a scanning mechanism configured to scan, on an object of observation, a condensing position of the laser light; and
a detector configured to detect signal light obtained through the scanning of the laser light within a time frame of a detection time, and convert the signal light that is detected into an electric signal, and
wherein the instructions, when executed by a computer, cause the computer to define a sampling time per one sampling by the detector by controlling the light source to perform a change in an irradiation time of the laser light within the time frame of the detection time, the irradiation time of the laser light being changed in accordance with a change in a scanning rate of scanning the condensing position of the laser light by the scanning mechanism.

* * * * *